United States Patent [19]
Kahan et al.

[11] Patent Number: 4,616,038
[45] Date of Patent: Oct. 7, 1986

[54] COMBINATION OF THIENAMYCIN-TYPE ANTIBIOTICS WITH DIPEPTIDASE INHIBITORS

[75] Inventors: Frederick M. Kahan, Scotch Plains; Helmut Kropp, Kenilworth, both of N.J.

[73] Assignee: Merck & Co., Inc., Rahway, N.J.

[21] Appl. No.: 747,750

[22] Filed: Jun. 24, 1985

Related U.S. Application Data

[63] Continuation of Ser. No. 340,152, Jan. 18, 1982, abandoned, which is a continuation-in-part of Ser. No. 187,929, Sep. 17, 1980, abandoned, which is a continuation-in-part of Ser. No. 50,232, Jun. 22, 1979, abandoned, which is a continuation-in-part of Ser. No. 927,213, Jul. 24, 1978, abandoned.

[51] Int. Cl.⁴ ............................................. A61K 31/195
[52] U.S. Cl. .................................................... 514/563
[58] Field of Search .......................................... 514/563

[56] References Cited

U.S. PATENT DOCUMENTS

| 2,460,708 | 2/1940 | Mozengo et al. | 260/534 |
| 3,032,581 | 5/1962 | Leonard | 260/471 |
| 3,949,000 | 4/1976 | Violet | 260/606.5 P |
| 4,008,281 | 2/1977 | Knowles et al. | 260/606.5 P |

OTHER PUBLICATIONS

Srinivasan et al., Tetrahedron Letters, No. 12, pp. 891–894 (1976).

Primary Examiner—Stanley J. Friedman
Attorney, Agent, or Firm—Robert J. North; Hesna J. Pfeiffer

[57] ABSTRACT

Antibacterial compositions of thienamycin-type compounds and a dipeptidase (E.C.3.4.13.11) inhibitor.

6 Claims, No Drawings

COMBINATION OF THIENAMYCIN-TYPE ANTIBIOTICS WITH DIPEPTIDASE INHIBITORS

RELATIONSHIP TO PRIOR APPLICATIONS

This application is a continuation of Ser. No. 340,152, filed Jan 18, 1982, now abandoned, which application is a continuation-in-part of U.S. Ser. No. 187,929, filed Sept. 17, 1980, now abandoned which was in turn a continuation-in-part of U.S. Ser. No. 50,232, filed June 22, 1979, now abandoned, which was in turn a continuation-in-part of U.S. Ser. No. 927,213, filed July 24, 1978, now abandoned.

INTRODUCTION

A new class of fused ring β-lactam antibiotics, including thienamycin and its semi-synthetic derivatives, epithienamycins, and olivanic acids, has recently been described. These compounds which will be defined more extensively below, are hereinafter referred to as the "thienamycin class of compounds". These compounds have a high level of antibacterial activity, but are subject to extensive metabolism by mammalian species.

The kidney was identified as the primary site of metabolism, and an enzyme was purified from renal extracts which catalyzed the inactivation of thienamycin by hydrolysis of the β-lactam. By such criteria as cytological localization, substrate specificity and susceptibility to enzyme inhibitors, this enzyme is very similar if not identical to a widely studied renal dipeptidase (E.C.3.4.13.11), also referred to in the literature as "dehydropeptidase-I". However, the β-lactamase activity is exhibited only toward the thienamycin class of compounds. Indeed, there exists no precedent example of the mammalian metabolism via β-lactam cleavage of any representative of the classical β-lactam antibiotics, the penicillins and cephalosporins.

DETAILED DESCRIPTION OF THE INVENTION: THIENAMYCINS

The term "thienamycin class of compounds" is used to identify any of a number of naturally occurring, semi-synthetic, or synthetic derivatives or analog compounds having a common fused-ring β-lactam nucleus. These compounds can be generically classed as 6- and (optionally) 2-substituted pen-2-em-3-carboxylic acids and 1-carbadethia-pen-2-em-3-carboxylic acids or 1-azabicyclo[3.2.0]hept-2-ene-7-one-2-carboxylic acids.

Some specific compounds particularly useful in this invention are represented structurally in the following formula I:

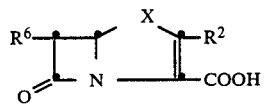

wherein X can be $CH_2$ or S; $R^2$ can be hydrogen; —S—alkyl of 1 to 6 carbons; —S—$CH_2CH_2NHR^3$, wherein $R^3$ is hydrogen, acetyl, formimidoyl, acetimidoyl; —S(O)—CH=CHNHCOCH$_3$ and —S—CH=CHNHCOCH$_3$; and $R^6$ is

wherein $R^7$ is hydrogen, hydroxy or sulfonyloxy, or $R^6$ is H. All possible stereoisomeric forms are included within the above structural definition.

All of these compounds within Formula I are described in the literature. When X is $CH_2$, and R is $SCH_2CH_2NH_2$, and $R^6$ is $CH(OH)CH_3$, the compound is known as thienamycin, an antibiotic produced by fermentation of S. cattleya, described and claimed in U.S. Pat. No. 3,950,357, issued Apr. 13, 1976. The N-substituted derivatives of thienamycin, i.e., in the formula I above wherein $R^3$ is other than hydrogen, are disclosed and claimed in co-pending U.S. applications and their published foreign equivalents. The fermentation product N-acetyl thienamycin ($R^6$ is $CH(OH)CH_3$, and $R^3$ is acetyl), also called 924A, is claimed in Belgian Pat. No. 848,346, issued May 16, 1977. The N-imidoyl derivatives are covered in Belgian Patent No. 848,545, issued May 20, 1977. The unsaturated side chain-containing compound, also called N-acetyldehydrothienamycin or 924A$_5$ is a fermentation product claimed in U.S. Pat. No. 4,162,323, issued July 24, 1979, and also in Belgian Pat. No. 866,035, issued Oct. 17, 1978. Epimeric forms of N-acetyl thienamycin, also called 890A$_1$ and 890A$_3$, as well as the desacetyl 890A$_1$ and desacetyl 890A$_3$ are disclosed, respectively in published French Pat. No. 7,634,887, granted Apr. 14, 1980, claiming priority of U.S. Ser. No. 634,300, filed Nov. 21, 1975, and Belgian Pat. No. 848,349, issued May 16, 1977. Epimeric forms of the unsaturated thienamycin, also called 890A$_2$ and 890A$_5$ are claimed in published French Pat. No. 7,711,891, granted Apr. 20, 1977. The 6-sulfonyloxy-containing N-acetyl compounds, also called 890A$_9$ or 890A$_{10}$, are claimed respectively, in published French Pat. No. 7,734,456, granted June 23, 1980, claiming priority of U.S. Ser. No. 742,947, filed Nov. 17, 1976, and published French Pat. No. 7,734,457, filed Nov. 16, 1977 claiming priority of U.S. Ser. No. 742,958 filed Nov. 17, 1976. Desacetyl analogues of 890A$_9$ and 890A$_{10}$ are respectively claimed in U.S. Ser. No. 767,723, filed Feb. 11, 1977, now abandoned, and its continuation U.S. Ser. No. 860,665, filed Dec. 15, 1977, now abandoned, and also in French Pat. No. 7,803,666 granted May 5, 1980; and U.S. Ser. No. 767,920, filed Feb. 11, 1977, now abandoned and its continuation U.S. Ser. No. 6,959, filed Jan. 25, 1979, now abandoned, and also in French Appln. No. 7,803,667, filed Feb. 9, 1978. Some of these latter compounds in the 890A$_9$ and 890A$_{10}$ series are also known as derivatives of olivanic acid (see Corbett et al., J. Chem. Soc. Chem. Commun. 1977, No. 24, pp. 953–54). Compounds of the Formula I above when $R^2$ is hydrogen, also called descysteaminyl thienamycins, are claimed in U.S. Ser. No. 668,898, filed Mar. 22, 1976, now abandoned, and its continuation-in-part, U.S. Ser. No. 847,297, filed Oct. 31, 1977, now abandoned, and also in Belgian Pat. 867,227, granted Nov. 20, 1978.

The compounds wherein $R^6$ is hydrogen, and X is $CH_2$, are disclosed in U.S. Ser. No. 843,171, filed Jan. 1, 1977, now abandoned, and in its granted Belgian equivalent No. 860,962, granted May 18, 1978

A thienamycin-type antibiotic in which $R^2$ is —$SCH_2CH_2NHAc$ and $R^6$ is $C_2H_5$, has been named PS-5 and is reported by K. Okaimura et. al., J. Antibiotics 31 p. 480 (1979), see also Belgian Pat. No. 865,578.

The compounds in which X is S, also called "penems", are described by R. B. Woodward in "Recent Advances in the Chemistry of β-Lactam Antibiotics", J. Elks (Ed), The Chemical Society, London, 1977, p. 167; R. B. Woodward, Abstracts of Uppsala University 500 Years Symposium on Current Topics in Drug Research, Uppsala, Sweden, Oct. 19-21, 1977, *Acta. Pharm, Suecica*, Vol. 14, Supplement, p. 23, and U.S. Pat. No. 4,070,477, issued Jan. 24, 1978 and U.S. Pat. No. 4,260,618 issued Apr. 7, 1981, and in British patent applications No. 2,013,674 published Aug. 15, 1979 and No. 2,042,520 published Sept. 24, 1980. The compounds wherein X is S are not limited to those encompassed by formula I above but include, in addition, all of the compounds disclosed in the references listed in this paragraph.

The disclosures of the foregoing patents, pending and abandoned patent applications and literature references are hereby incorporated by reference.

Particularly preferred members within the thienamycin class of compounds are the N-formimidoyl and N-acetamidoyl derivatives of thienamycin. The crystalline form of N-formimidoyl thienamycin, which has recently been described, is also useful in the practice of this invention. An example illustrating a preferred way of making this compound follows:

ILLUSTRATIVE EXAMPLE

N-Formimidoyl thienamycin, (NFT) crystalline

Step A. Benzylformimidate hydrochloride

A 3 l. three-necked flask fitted with an addition funnel, overhead stirrer, and a reflux condenser, was charged with a mixture of benzyl alcohol (125 g., 1.15 mol) formamide (51 g., 1.12 mol) and anhydrous ether (1200 ml.). The mixture was stirred vigorously at room temperature (20°-25° C.) under a nitrogen atmosphere and benzoyl chloride (157 g., 1.12 mol) in 50 ml. of anhydrous ether was added dropwise using the addition funnel. The addition required approximately 50 minutes.

The reaction mixture was stirred an additional 60 minutes room temperature. The ether was removed by decantation and 300 ml. of acetic anhydride in 500 ml. of anhydrous ether was added. The mixture was stirred 30 minutes at room temperature. The precipitate was allowed to settle and the etheracetic anhydride was again removed by decantation. The solid was collected by filtration, washed with 500 ml. of ether and dried in vacuo over KOH at 25° C. for 2 hrs. to give 130 g. (67%) of benzylformimidate hydrochloride as a white solid.

The product was assayed by NMRδ (DMSO) 5.7 (s, 2H, φCH$_2$), 7.5 (s, 5H, φ), 9.0 (s, 1H, HC=N). The product is thermally unstable. It decomposes to formamide and benzyl chloride at 0° C. and above. However, no appreciable decomposition was detected on storage at −20° C. for 2 months.

Step B. Derivatization of Thienamycin

Thienamycin (in the form of a 6 l. aqueous solution, pH=6.5, concentrate from the fermentation broth, containing 28 g. thienamycin) was placed in a large beaker (12 l) and cooled to 0° C. The beaker was equipped with a pH meter and an efficient high speed stirrer. The pH was raised to 8.5 by the careful addition of 3N KOH (KOH was added dropwise via syringe to the stirred solution). The solution was treated with 6 equivalents of solid benzyl formimidate hydrochloride (~100 g.) in portions while maintaining the pH at 8.5 ±0.3 by the addition of 3N KOH (200 ml.) using a syringe. The addition required 3-5 min. The reaction mixture was stirred for 6 min. at 0° C. and then assayed by liquid chromatography to insure completion of the reaction. The solution was adjusted to pH 7 with 1N HCl. The volume of the reaction mixture was measured, and the solution was assayed by UV. The neutralized reaction mixture was concentrated to 15 g./l. on the reverse osmosis unit at <10° C. The volume of the concentrate was measured and the pH was adjusted to 7.2-7.4, if necessary. The concentrate was filtered through a medium porosity sintered glass funnel to remove any solids present after concentration.

Step C. Dowex 50W×2 Chromatography

The concentrate (750-1000 ml., 15-20 g.) was applied to 0° C. to a precooled 18 l. column of Dowex 50W×2 in the potassium cycle (200-400 mesh resin) and the column was eluted at 0°-5° C. with distilled deionized water a flow rate of 90 ml/min. and a head pressure of 0-45 psig.

Forerun fractions of 4 l., 2 l., and one l., were collected followed by 18 fractions of 450 ml. each, and one final fraction of 2 l. Each fraction was assayed by UV (1/100 dilution, NH$_2$OH extinction was omitted) and the total amount of NFT present in each fraction was calculated. The beginning and end fractions were assayed for liquid chromatography purity and the desired rich cut fractions were combined. The pH of the combined rich cuts was determined by both pH meter and bromothymol blue indicating solutions and was adjusted to pH 7.2-7.4 if necessary. The combined rich cuts (3-4 l.) were then assayed by UV and the total formamidine content was determined, 15-16 g., 75% yield from the column. The rich cuts were concentrated on the reverse osmosis unit at <10° C. as far as possible, then the concentration to 33 g./l. was completed on the circulatory evaporator at less than 28° C. A total volume of about 500 ml. concentrate was obtained

Step D. Crystallization of N-Formimidoyl Thienamycin

The concentrate from the previous step is adjusted to 7.3, if necessary, and N-formimidoyl thienamycin content assayed by UV, was about 85-90%. The concentrate was filtered through a sintered glass funnel (medium porosity) into a large Erlenmeyer flask. Five volumes (~2200 ml.) of 3A ethanol was filtered into the concentrate and the solution was stirred at room temperature for 10 minutes and at 0° C. for 12-24 hrs.

The crystals were filtered by suction filtration and washed with 0.1 volume (~250 ml.) of 0° C. 80% 3A ethanol followed by 1/25 volume (100 ml ) of 3A ethanol at room temperature. The crystals were dried in vacuo for 12-24 hrs. to give approximately a 40% over-all yield of N-formimidoyl thienamycin (10-12 g.).

Analytical results on a 50 g. blend of N-formimidoyl thienamycin, prepared as above, are as follows: C, theory 45.42%; found, 45.82%. H, theory 6.03%; found, 5.72%. N, theory 13.24%; found, 13.10%. S, theory 10.10%; found, 10.14%. residue on ignition, predicted: 0.5, found 0.47%; $[\alpha]_D^{25} = 89.4°$, T.G.=6.8%, UV λmax 300 MM, E %=328.

DETAILED DESCRIPTION OF THE INVENTION DIPEPTIDASE INHIBITORS

The chemical substances which selectively inhibit the metabolism of the dipeptidase [E.C.3.4.13.11], also called "dipeptidase inhibitors", include chemical compounds which are Z-2-acylamino-3-monosubstituted propenoates having the following formula

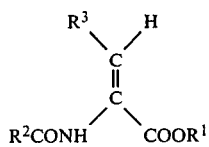

wherein $R^2$ and $R^3$ are hydrocarbon radicals in the range respectively of 3-10 and 1-15 carbon atoms. In either of these hydrocarbon radicals $R^2$ and $R^3$, up to 6 hydrogens may be replaced by halogens, or a non-terminal methylene may be replaced by oxygen or sulfur, including oxidized forms of the latter.

A terminal hydrogen in $R^3$ can also be replaced by a hydroxyl or thiol group, which may be acylated, such as with an alkanoyl acid of 1-8 carbon atoms, or carbamoylated, including alkyl and dialkyl carbamate derivatives; or the hydrogen can be replaced by an amino group, which may be derivatized as in an acylamino, ureido, amidino, guanidino, or alkyl or substituted alkyl amino group, including quaternary nitrogen groupings; or, alternatively, there may be replacement by acid groups such as carboxylic, phosphonic or sulfonic acid groups or esters or amides thereof, as well as cyano; or combinations thereof, such as a terminal amino acid grouping.

$R^2$ is preferably a branched alkyl or cycloalkyl radical ($C_{3-10}$), with a limitation that the carbon adjacent to the carbonyl cannot be tertiary. $R^2$ cannot be phenyl or straight chain loweralkyl of 1-4 carbon atoms, where $R^3$ is straight chain lower alkyl of 1-4 carbon atoms. $R^1$ is hydrogen, loweralkyl ($C_{1-6}$) or dialkylaminoalkyl (e.g., $-CH_2CH_2N(C_2H_5)_2$, $-CH_2CH(CH_3)N(CH_3)_2$.

Some of the compounds with formula II above have asymmetric forms. Racemic Z-2-(2,2-dimethylcyclopropanecarboxamido)-2-octenoic acid has been resolved. The activity resides in the dextrorotatory isomer, which has the S-configuration.

Within the definition of $R^2$, the following sub-groups are included $$-R^4 \qquad \text{II A}$$

wherein $R^4$ is a straight, branched, or cyclic hydrocarbon radical of 3-10 carbon atoms which may be substituted as specified above in the definition of $R^2$;

$$-R^5R^6 \qquad \text{II B}$$

wherein $R^5$ is cycloalkyl of 3-6 carbon atoms and $R^6$ is either 1 or 2 alkyl substituents which may be joined to form another ring on the cycloalkyl group, or $R^5$ and $R^6$ may be substituted as specified above in the definition of $R^2$;

$$-R^7R^8 \qquad \text{II C}$$

wherein $R^7$ is an alkylene group of 1-3 carbon atoms and $R^8$ is cycloalkyl of 3-6 carbon atoms which may be substituted as specified above in the definitions of $R^2$ and $R^3$;

within these sub-groups, the following specific compounds are included:

II A: Z-2-isovaleramido-2-pentenoic acid; methyl Z-2-isovaleramido-2-butenoate; Z-2-isovaleramido-2-butenoic acid; Z-2-benzamido-2-butenoic acid; Z-2-(3,5,5-trimethylhexanamido)-2-butenoic acid; Z-2-cyclobutanecarboxamido-2-butenoic acid; Z-2-cyclopropanecarboxamido-2-butenoic acid; Z-2-cyclopropanecarboxamido-2-pentenoic acid; Z-2-(3-methylvaleramido)-2-butenoic acid; Z-2-cycloheptanecarboxamido-2-butenoic acid; Z-2-nonanamido-2-butenoic acid; Z-2-cyclohexanecarboxamido-2-butenoic acid; Z-2-(4-methylvaleramido)-2-butenoic acid; Z-2-t-butylacetamido-2-butenoic acid; Z-2-octanamido-2-butenoic acid; Z-2-butyramido-2-butenoic acid; Z-2-valeramido-2-butenoic acid; Z-2-valeramido-2-pentenoic acid; Z-2-cyclopentanecarboxamido-2-butenoic acid; Z-2-(6-methylheptanamido)-2-butenoic acid; Z-2-hexanamido-2-butenoic acid; Z-2-(3,7-dimethyloctanamido)-2-butenoic acid; Z-2-(3,7-dimethyl-6-octenamido)-2-butenoic acid; Z-2-(5-chlorovaleramido)-2-butenoic acid; Z-2-(3-chlorobenzoylamido)-2-butenoic acid; Z-2-(2-chlorobenzamido)-2-butenoic acid; Z-2-nonanamido-2-butenoic acid; Z-2-(6-bromohexanamido)-2-butenoic acid; Z-2-(3,3-dimethylpropenamido)-2-butenoic acid; Z-2-benzamido-2-cinnamic acid; Z-2-benzamido-2-pentenoic acid; Z-2-benzamido-5-methoxy-2-pentenoic acid; Z-2-benzamido-2-hexenedioic acid; Z--isovaleramido-2-octenoic acid; Z-2-isovaleramido-2-cinnamic acid; Z-2-isovaleramido-2-hexenedioic acid; Z-2-cyclopropanecarboxamido-2-cinnamic acid; Z-2-cyclopropanecarboxamido-2-hexenedioic acid; Z-2-(5-methoxy-3-methylvaleramido)-2-butenoic acid; Z-2-ethylthioacetamido-2-butenoic acid; Z-2-(2,2-dichlorocyclopropanecarboxamido)-2-butenoic acid; Z-2-(2-ethylhexanamido)-2-butenoic acid; Z-2-di-n-propylacetamido-2-butenoic acid;

II B: Z-2-(2,2-dimethylcyclopropanecarboxamido)-2-butenoic acid; (+)-Z-2-(2,2-dimethylcyclopropanecarboxamido)-2-butenoic acid; Z-2-(2,2-dimethylcyclopropanecarboxamido)-2-pentenoic acid; Z-2-(2,2-dimethylcyclopropanecarboxamido)-2-octenoic acid; Z-2-(2,2-dimethylcyclopropanecarboxamido)-2-hexenoic acid; Z-2-(2,2-dimethylcyclopropanecarboxamido)-2-cinnamic acid; Z-2-(2,2-dimethylcyclopropanecarboxamido)-5-methoxy-2-pentenoic acid; Z-2-(2,2-dimethylcyclopropanecarboxamido)-4,4,4-trifluoro-2-butenoic acid; Z-2-(2,2-dimethylcyclopropanecarboxamido)-3-(2-chlorophenyl)propenoic acid; Z-2-(2,2-dimethylcyclopropanecarboxamido)-2-hexenedioic acid; Z-2-(2-ethylcyclopropanecarboxamido)-2-butenoic acid; Z-2-(2,2-diethylcyclopropanecarboxamido)-2-butenoic acid; Z-2-(2,2-diethylcyclopropanecarboxamido)-2-pentenoic acid; Z-2-(2-isopropyl-2-methylcyclopropanecarboxamido)-2-butenoic acid; Z-2-(2-methylcyclohexanecarboxamido)-2-butenoic acid; Z-5-cyano-2-(2,2-dimethylcyclopropanecarboxamido)-2-pentenoic acid; Z-5-(N,N-dimethylcarbamoyl)-2-(2,2-dimethylcyclopropanecarboxamido)-2-pentenoic acid; Z-2-(2,2-dimethylcyclopropanecarboxamido)-5-methanesulfonyl-2-pentenoic acid; Z-2-(2,2-dimethylcyclopropanecarboxamido)-5-ethoxycarbonyl-2-pentenoic acid; Z-2-(2-methylcyclopropanecarboxamido)-2-butenoic acid; methyl Z-2-(2,2-dimethylcyclopropanecarboxamido)-2-butenoate; ethyl Z-2-(2,2-dimethylcyclopropanecarboxamido)-2-butenoate; 2-dimethylaminoethyl ester of Z-2-(2,2-dimethylcyclopropanecarboxamido)-2-butenoic acid; 3-diethylaminoproyl ester of Z-2-(2,2-dimethylcyclopropanecarboxamido)-2-pentenoic acid; Z-2-(2,3-dimethylcyclopropanecarboxamido)-2-butenoic acid; Z-2-(3,3-dimethylcyclobutanecarboxamido)-2-butenoic acid; Z-2-(2-spirocyclopentanecarboxamido)-2-butenoic acid; Z-2-(2-t-butyl-3,3-dimethylcyclopropanecarboxamido)-2-butenoic acid; Z-2-(2,2-dimethylcyclopropanecarboxamido)-4-methyl-2-pentenoic acid; Z-2-(2-t-butylcyclopropanecarboxamido)-2-butenoic acid; Z-2-(2-phenylcyclopropanecarboxamido)-2-butenoic acid; Z-3-cyclohexyl2-(2,2-dimethylcyclopropanecarboxamido)propenoic acid; Z-5-carboxy-5-(2,2-dimethylcyclopropanecarboxamido)-4-pentenamidine; Z-5-dimethyl amino-2-(2,2-dimethylcyclopropanecarboxamido)-2-pentenoic acid; Z-3-cyclopropyl-2-(2,2-dimethylcyclopropanecarboxamido)propenoic acid; Z-2-(2,2-dimethylcyclopropanecarboxamido)-2,5-hexadienoic acid; Z-2-(2,2-dimethylcyclopropanecarboxamido)-4-phenyl-2-butenoic acid; Z-2-(2,2-dimethylcyclopropanecarboxamido)-6-mercapto-2-hexenoic acid; Z-2-(2,2-dimethylcyclopropanecarboxamido)-5-methylthio-2-pentenoic acid; Z-2-(2,2-dimethylcyclopropanecarboxamido)-5-phosphono-2-pentenoic acid; Z-2-(2,2-dimethylcyclopropanecarboxamido)-2-heptenoic acid; Z-2-(2,2-dimethylcyclopropanecarboxamido)-5-phenyl-2-pentenoic acid; Z-2-(2,2-dimethylcyclopropanecarboxamido)-2-nonenoic acid; Z-2-(2,2-dimethylcyclopropanecarboxamido)-2-decenoic acid; Z-2-(2,2-dimethylcyclopropanecarboxamido)-2-tridecenoic acid; Z-2-(2,2-dimethylcyclopropanecarboxamido)-6-methoxy-2-hexenoic acid (and 5-methoxy-2-pentenoic acid); Z-2-(2,2-dimethylcyclopropanecarboxamido)-6-methyl-2-heptenoic acid; Z-4-cyclohexyl-2-(2,2-dimethylcyclopropanecarboxamido)-2-butenoic acid;

II C: Z-2-cyclobutylacetamido-2-butenoic acid; Z-2-cyclopentylacetamido-2-butenoic acid; Z-2-cyclohexylacetamido-2-butenoic acid; Z-2-(4-cyclohexylbutyramido)-2-butenoic acid; Z-2-cyclopropylacetamido-2-butenoic acid; Z-2-cyclopropylacetamido-2-pentenoic acid; Z-2-(3-cyclopentylpropionamido)-2-butenoic acid; Z-2-(3-cyclohexylpropionamido)-2-butenoic acid; Z-2-(4-(2-thienyl)-butyramido)-2-butenoic acid; Z-2-(4-phenyl-butyramido)-2-butenoic (D,L-α-lipoamido)-2-pentenoic acid; Z-2-(D,L-α-lipoamido)-2-cinnamic acid; Z-2-(3-(2-tetrahydrofuryl)-propionamido)-2-butenoic acid.

Particularly preferred substituents within the definition of $R^2$ above include the 2,2-dimethylcyclopropyl and the 2,2-dichlorocyclopropyl groups.

Within the definition of $R^3$, particularly preferred groups of compounds include n-alkyl (1–9 carbons) and n-alkyl (1–9 carbons) having a terminal substituent which is a quaternary nitrogen, amine derivative, or amino acid derived group.

By the term "quaternary nitrogen" is meant a tetrasubstituted or heteroaromatic nitrogen which is positively charged. An ammonium moiety, substituted with hydrocarbon groups having 1-7 carbon atoms, which can be the same or different, is signified.

By the term "amino derivative" is meant a group such as amino, acylamino, ureido, amidino, guanidino and alkyl (1–7 carbon atoms) derivatives thereof.

By the term "amino acid derived group" is meant a moiety such as cysteinyl (—SCH$_2$CH(NH$_2$)COOH) or sarcosyl (—N(CH$_3$)CH$_2$COOH) in which a hydrogen joined to O, N or S of known amino acids is replaced.

Particularly preferred compounds from the most preferred groups of substituents of $R^2$ and R are those wherein $R^2$ is 2,2-dimethylcyclopropyl or 2,2-dichlorocyclopropyl, and $R^3$ is a hydrocarbon chain of 3 to 7 carbon atoms without a terminal substituent, or having a terminal substituent which is trimethylammonium, amidino, guanidino, or 2-amino-2-carboxyethylthio. Names of specific examples of these include:

Z-2-(2,2-dimethylcyclopropanecarboxamido)-8-trimethylammonium hydroxide-2-octenoic acid inner salt;
Z-2-(2,2-dichlorocyclopropanecarboxamido)-8-trimethylammonium hydroxide-2-octenoic acid inner salt;
Z-2-(2,2-dimethylcyclopropanecarboxamido)-8-formamidino-2-octenoic acid;
Z-2-(2,2-dimethylcycloprpanecarboxamido)-8-guanidino-2-octenoic acid;
Z-2-(2,2-dimethylcyclopropanecarboxamido)-8-ureido-2-octenoic acid;
Z-8-(L-2-amino-2-carboxyethylthio)-2-(2,2-dimethylcyclopropanecarboxamido)-2-octenoic acid;
Z-2-(2,2-dimethylcyclopropanecarboxamido)-2-octenoic acid (racemic and dextrorotatory forms);
Z-2-(2,2-dichlorocyclopropanecarboxamido)-2-octenoic acid;
7-(L-2-amino-2-carboxyethylthio)-2-(2,2-dimethylcyclopropanecarboxamido)-2-heptenoic acid; and
6-(L-2-amino-2-carboxyethylthio)-2-(2,2-dimethylcyclopropanecarboxamido)-2-hexenoic acid.

The Z configuration (J. E. Blackwood et al., *J. Am. Chem. Soc.*, 90, p. 509 (1968)) is assigned to the above compounds on the basis of their NMR spectra by analogy with the work of A. Srinavasan et al. [*Tetrahedron Lett.*, 891 (1976)].

Although these compounds of Formula II, when $R^1$ is H, are described and named as the free acids, it will be apparent to one skilled in the art that various pharmaceutically acceptable derivatives such as alkali and alkaline earth metal, ammonium, or amine salts, or the like can be employed as equivalents thereto. Salts such as the sodium, potassium, calcium, or tetramethylammonium salts are suitable.

Some of the compounds of Formula II are novel compounds which are claimed in a copending U.S. application, U.S. Ser. No 927,212, filed on July 24, 1978, now abandoned, and in U.S. Ser. No. 50,233, filed June 22, 1979, now abandoned; and in Case 16140IB, U.S. Ser. No. 188,178, filed concurrently herewith, and which do not form part of this invention.

As mentioned above, the thienamycin-type compound is used in combination with the dipeptidase inhibitor.

METHODS OF TESTING AND USING THE INVENTION

As noted, disposition studies with thienamycin, its natural analogs and its semi-synthetic derivatives have revealed a major metabolic degradation pathway of elimination in the various species examined (mouse, rat, dog, chimpanzee, Rhesus monkey). The extent of metabolism is reflected in low urinary recovery and short plasma half-lives. The nature of this degradation was demonstrated to be lactam cleavage by the renal dipeptidase (E.C.3.4.13.11), described first by Bergmann, M. and Schleich, H., *Z. Physiol. Chem.*, 205 65 (1932); see also Greenstein, J. P., *Advances in Enzymology*, Vol. VIII, Wiley-Interscience, (1948), New York, and Campbell, B. J.; Lin, Y-C., Davis, R. V. and Ballew, E., "The Purification and Properties of Particulate Renal Dipeptidase", *Biochim. Biophys. Acta.*, 118, 371 (1966).

In order to demonstrate the ability of the compounds of Formula II to suppress the action of the renal dipeptidase enzyme, an in vitro screen procedure was followed. This measured the ability of compounds to inhibit hydrolysis of glycyldehydrophenylalanine (GDP) by a solubilized preparation of dipeptidase isolated from hog kidneys The procedure is as follows to a 1 ml. system containing 50 mM "MOPS" (3-(N-morpholino)-propanesulfonic acid) buffer, pH 7.1, is added 5 μg of lyophilized enzyme, and the test compound at a final concentration of 0.1 mM. After a five minute incubation at 37° C., GDP is added to a final concentration of 0.05 mM. Incubation is continued for 10 minutes, at 37° C. and hydrolysis of GDP is measured by the change in optical density with time at 275 nm. Inhibition of the enzyme is gauged by comparison to a standard run containing no inhibitor and is expressed as the inhibitor binding constant, $K_i$. This is the concentration of the inhibitor which achieves 50% inhibition of enzyme.

The substrate GDP is employed in preference to thienamycin in this screen because it has a much higher maximal velocity of hydrolysis by renal dipeptidase, thereby reducing the amount of enzyme required. Both GDP and thienamycin have a similar affinity for renal dipeptidase; furthermore, $K_i$'s of inhibitors tested have been identical for the two substrates.

In addition to this in vitro screen procedure, an in vivo sreen was followed to measure the test compound's ability to inhibit metabolism as reflected by increase in urinary recovery of thienamycin from the mouse. The procedure involves co-administration of the test compound by the intravenous or subcutaneous route at a dose-rate of 10-100 mg/kg, with 10 mg/kg thienamycin. Thienamycin recovery in the urine over a 4 hour period is then compared with its recovery in a control group to which test compound was not coadministered.

Urinary recovery of thienamycin was measured in all cases with the use of a cylinder or disc diffusion assay, conducted in a manner described in U.S. Pat. No. 3,950,357. This bioassay, with *Staphylococcus aureus* ATCC 6538 as the test organism, has a useful response range from 0.04 μg/ml to 3.0 μg/ml.

The combination of the inhibitor and the thienamycin class compound can be in the form of a pharmaceutical composition containing the two compounds in a pharmaceutically acceptable carrier. The two can be employed in amounts so that the weight ratio of the thienamycin class compound to inhibitor is 1:3 to 30:1, and preferably 1:1 to 5:1.

The components can also be separately administered. For instance, the thienamycin class compound can be administered intramuscularly or intravenously in amounts of 1-100 mg/kg/day, preferably 1-20 mg/kg/day, or 1-5 mg/kg/day, in divided dosage forms, e.g., three or four times a day. The inhibitor can be separately administered, orally, intramuscularly, or IV, in amounts of 1-100 mg/kg/day, or preferably 1-30 mg/kg/day, or 1-5 mg/kg/day. The amounts of the two components administered during one day ideally are within the ratio limits denoted above.

One preferred dosage level known to applicants is as a single dose, of two crystalline compounds, one being N-formimidoyl thienamycin and the other being (+) Z-2-(2,2-dimethylcyclopropanecarboxamido)-2-octenoic acid, co-administered in a sterile aqueous IV injection form (sodium salt), at a level of 150 mg. of the thienamycin and either 75 or 150 mg of the octenoic acid. This dose is given to humans (each assumed to weigh about 80 kg.) from 1 to 4 times a day, or 2-8 mg/kg/day of the thienamycin class compound and 1-8 mg/kg/day of the inhibitor.

The most preferred dosage regimen and level is the combination of crystalline N-formimidoyl thienamycin and the other being the crystalline form of 7-(L-amino-2-carboxyethylthio)-2-(2,2-dimethylcyclopropanecarboxamido)-2-heptenoic acid, co-administered in a sterile aqueous IV injection form (sodium salt), at a level of 250 or 500 mg of the thienamycin and about 1:1 (weight) of the heptenoic acid, or 250 or 500 mg. This dose is given to humans (each assumed to weight about 80 kg.) from 1 to 4 times daily, or 3.1-25 mg/kg/day of each drug.

The components, whether administered separately or together are employed in pharmaceutically acceptable carriers such as conventional vehicles adapted for oral adminstration such as capsules, tablets, or liquid solutions or suspensions. The components separately or together, can also be dissolved in a vehicle adapted for administration by injection. Suitable formulations for oral use, may include diluents, granulating agents, preservatives, binders, flavoring agents, and coating agents. The example of an oral use composition in the combination of active ingredients, or the acid component alone, intermixed in the dry pulverulent state with gelatin, starch, magnesium stearate, and alginic acid, and pressed into a tablet As noted above, the presently known preferred method is parenteral administration of the thienamycin class compound and either co-parenteral administration or oral administration of the inhibitor compound.

Examples which illustrate this invention follow.

Section 1. Examples Illustrating Activity

EXAMPLE 1

In Vitro Test Data

A 1 ml. system of 50 mM "MOPS" buffer, pH 7.1, is used. To this is added 5 μg of the pig renal enzyme and an amount of the test compound to bring its final concentration to 0.1 mM. After a five minute incubation at 37° C., an amount of GDP is added to bring its final concentration to 0.05 mM. The system is again incubated for 10 minutes, at 37° C. Hydrolysis of GDP is measured by its change in optical density with time at 275 nm. Inhibition of the enzyme is gauged by comparison to a standard run containing no inhibitor and is presented as percent inhibition. The $K_i$ is a constant indicating the concentration of inhibitor necessary to produce 50% inhibition of enzyme. It is a calculated value obtained from running multiple in vitro assays, as above, at concentrations resulting in inhibition below and above the 50% inhibition point. The results are presented in Table I.

TABLE I

Compounds $$R^3-\underset{H}{C}=\underset{NHCOR^2}{\overset{COOH}{C}}$$

| Dipeptidase Inhibitor | $R^3$ | $R^2$ | % Inhibition at $10^{-4}$ M | $K_i$ ($\mu$M) |
|---|---|---|---|---|
| 1 | CH$_2$CH$_3$ | cyclopropyl with two CH$_3$ groups on same carbon | 98 | 0.18 |
| 2* | CH$_3$ | cyclopropyl with two CH$_3$ groups on same carbon | 98 | 0.39 |
| 2a* | CH$_3$ | cyclopropyl with two CH$_3$ groups on same carbon | 100 | 0.12 |
| 2b* | CH$_3$ | cyclopropyl with two CH$_3$ groups on same carbon | | 19.8 |
| 3 | CH$_3$ | cyclopropyl with CH$_3$ | 92 | 1.7 |
| 4 | CH$_2$CH$_3$ | $-CH_2-CH(CH_3)_2$ | 87 | 3.2 |
| 5 | CH$_3$ | $-CH_2CH(CH_3)-CH_2C(CH_3)_3$ | 81 | 4.4 |
| 6 | CH$_3$ | cyclopropyl with two CH$_3$ groups on adjacent carbons | 83 | 4.6 |
| 7 | CH$_3$ | $-CH_2-CH(CH_3)_2$ | 91 | 6 |
| 8 | CH$_3$ | cyclobutyl | 80 | 6.2 |
| 9 | CH$_3$ | $-CH_2-$cyclobutyl | 83 | 6.6 |
| 10 | CH$_3$ | cyclopropyl | 97 | 9 |
| 11 | CH$_3$ | $-CH_2-CH(CH_3)-CH_2CH_3$ | 82 | 10 |
| 12 | $-(CH_2)_4CH_2$ | cyclopropyl with two Cl groups on same carbon | | 0.059 |

TABLE I-continued

Compounds
$$R^3-C=C-NHCOR^2$$
with H and COOH on the central carbons

| Dipeptidase Inhibitor | $R^3$ | $R^2$ | % Inhibition at $10^{-4}$ M | $K_i$ ($\mu$M) |
|---|---|---|---|---|
| 13 | $-(CH_2)_5N^+(CH_3)_3$ | cyclopropyl-CCl$_2$ | | 0.18 |
| 14 | $-(CH_2)_5N^+(CH_3)_3$ | cyclopropyl-C(CH$_3$)$_2$ | | 1.11 |
| 15 | $-(CH_2)_5-NH-C(CH_3)=NH$ | cyclopropyl-C(CH$_3$)$_2$ | | 0.72 |
| 16 | $-(CH_2)_5-NH-C(=NH)-N(CH_3)_2$ | cyclopropyl-C(CH$_3$)$_2$ | | 0.89 |
| 17 | $-(CH_2)_4-S-CH_2-CH(NH_3^+)-COO^-$ | cyclopropyl-C(CH$_3$)$_2$ | | 0.21 |
| 18 | $CH_3$ | $-CH_2C(CH_3)_3$ | 75 | 20 |
| 19 | $CH_3$ | $-(CH_2)_6CH_3$ | 72 | 26 |
| 20 | $CH_3$ | $-(CH_2)_2CH_3$ | 69 | 30 |
| 21 | $CH_3$ | $-(CH_2)_3$-cyclohexyl | 68 | 30 |
| 22 | $CH_3$ | $-CH_2$-cyclopropyl | 64 | 22 |
| 23 | $CH_3$ | $(CH_2)_3CH_3$ | 64 | 32 |
| 24 | $CH_3$ | cyclopentyl | 59 | 30 |
| 25 | $CH_3$ | $-(CH_2)_4CH(CH_3)_2$ | 57 | |
| 26 | $CH_3$ | $-CH_2CH_2$-cyclopentyl | 56 | |
| 27 | $CH_3$ | $-CH_2CH_2$-cyclohexyl | 54 | |
| 28 | $CH_3$ | $-CH_2-(CH_2)_3CH_3$ | 54 | 39 |
| 29 | $CH_3$ | $-(CH_2)_5CH_3$ | 49 | |
| 30 | $CH_3$ | $-CH(CH_2CH_3)CH_2CH_2CH_2CH_3$ | 33 | |
| 31 | $CH_3$ | $-CH(CH_2CH_2CH_3)_2$ | 13 | |
| 32 | $CH_3$ | $-CH(CH_3)_2$ | 31 | |
| 33 | $HOO-CH_2CH_2$ | cyclopropyl | 90 | 5 |

TABLE I-continued

Compounds $$R^3-\underset{H}{C}=\underset{NHCOR^2}{\overset{COOH}{C}}$$

| Dipeptidase Inhibitor | R³ | R² | % Inhibition at 10⁻⁴ M | K_i (μM) |
|---|---|---|---|---|
| 34 | CH₃ | —CH₂—CH(CH₃)—CH₂CH₂OCH₃ | 88 | 9 |
| 35 | CH₃ | CH₂CH₂CH₂CH₂CH₂Br | 70 | 19 |
| 36 | CH₃ | CH₂CH₂CH₂CH₂Cl | 64 | 20 |
| 37 | CH₃ | CH₂CH₂CH₂—C₆H₅ | 72 | 11 |
| 38 | CH₃ | cyclopropyl-C(CH₃)₃ | 90 | 6.5 |
| 39 | CH₃(CH₂)₄ | CH₂—CH(CH₃)₂ | 95 | 2.6 |
| 40 | CH₃ | cyclopropyl-C(CH₃)(CH₂CH₃) | 100 | 0.45 |
| 41 | (CH₃)₂CH | cyclopropyl-C(CH₃)₂ | 98 | 0.54 |
| 42 | CH₃ | cyclopropyl-C(CH₂CH₃)₂ | 98 | 0.86 |
| 43 | CH₃ | cyclopropyl-CH₂CH₃ | 96 | 1.6 |
| 44 | CH₃ | cyclopropyl-C(CH₃)(CH(CH₃)₂) | 95 | 3 |
| 45 | CH₃CH₂ | cyclopropyl-C(CH₃)₂ | 98 | 0.18 |

TABLE I-continued

Compounds $$R^3-\underset{H}{C}=\underset{NHCOR^2}{\overset{COOH}{C}}$$

| Dipeptidase Inhibitor | R³ | R² | % Inhibition at $10^{-4}$ M | $K_i$ (μM) |
|---|---|---|---|---|
| 46 | Ph | —C(CH₃)₂-cyclopropyl | 100 | 0.62 |
| 47 | CH₃CH₂CH₂ | —C(CH₃)₂-cyclopropyl | 98 | 0.11 |
| 48 | (CH₃)₂CHCH₂ | —C(CH₃)₂-cyclopropyl | 97 | 0.23 |
| 49 | CH₃(CH₂)₃ | —C(CH₃)₂-cyclopropyl | 100 | 0.11 |
| 50 | CH₃(CH₂)₄ | —C(CH₃)₂-cyclopropyl | 100 | 0.17 |
| 51 | HOOCCH₂CH₂ | —C(CH₃)₂-cyclopropyl | 98 | 0.145 |
| 52 | cyclohexyl-CH₂ | —C(CH₃)₂-cyclopropyl | 100 | 0.15 |
| 53 | PhCH₂CH₂ | —C(CH₃)₂-cyclopropyl | 96 | 0.33 |
| 54 | CH₃SCH₂CH₂ | —C(CH₃)₂-cyclopropyl | 99 | 0.12 |

TABLE I-continued

Compounds $$\underset{R^3-C=C-NHCOR^2}{\overset{H\phantom{xxx}COOH}{|}}$$

| Dipeptidase Inhibitor | $R^3$ | $R^2$ | % Inhibition at $10^{-4}$ M | $K_i$ ($\mu$M) |
|---|---|---|---|---|
| 55 | $CH_3SO_2CH_2CH_2$ | ◁−C(CH_3)_2 | 96 | 0.5 |
| 56 | $CH_3(CH_2)_5$ | ◁−C(CH_3)_2 | 98 | 0.149 |
| 57 | $CH_3(CH_2)_6$ | ◁−C(CH_3)_2 | 99 | 0.092 |
| 58 | $CH_3(CH_2)_9$ | ◁−C(CH_3)_2 | 96 | 0.14 |
| 59 | $PhCH_2$ | ◁−C(CH_3)_2 | 98 | 0.44 |
| 60 | $CH_3O(CH_2)_3$ | ◁−C(CH_3)_2 | | 0.28 |
| 61 | $CH_3OCH_2CH_2$ | ◁−C(CH_3)_2 | 98 | 0.32 |
| 62 | $(CH_3)_3CCH_2$ | ◁−C(CH_3)_2 | | 0.34 |
| 63 | $(CH_3)_2CHCH_2CH_2$ | ◁−C(CH_3)_2 | 98 | 0.15 |

TABLE I-continued

Compounds $$R^3-\underset{H}{C}=\underset{|}{\overset{COOH}{C}}-NHCOR^2$$

| Dipeptidase Inhibitor | $R^3$ | $R^2$ | % Inhibition at $10^{-4}$ M | $K_i$ ($\mu$M) |
|---|---|---|---|---|
| 64 | $H_2OC(CH_2)_3$ | cyclopropyl with two CH_3 | 99 | 0.048 |
| 65 | tetrahydrofuranyl-CH_2 | cyclopropyl with two CH_3 | | 0.39 |
| 66 | $CH_3(CH_2)_4$ | (+) cyclopropyl with two CH_3 | | .08 |

*Compounds 2, 2a, and 2b are the racemic, dextrorotatory and levorotatory forms respectively.

EXAMPLE 2

In Vivo Test Data

An in vivo assay on the mouse was conducted as follows: 20 g Charles River CD, female mice were injected subcutaneously with the chosen dose of the chemical inhibitor. About two minutes later, the dose of thienamycin was given intravenously. A control of thienamycin above was also conducted. The level of thienamycin in the urine as a % of dose was measured using a bioassay technique. Results are found in Table II. The two test compound numbers are those from Table I. Compound 7 is Z-2-isovaleramido-2-butenoic acid; compound 10 is Z-2-cyclopropylcarboxamido-2-butenoic acid.

TABLE II

| Compound | Dose, mg/kg Compound | Dose, mg/kg Thienamycin | % Urinary Recovery of Thienamycin |
|---|---|---|---|
| 7 | 50 | 10 | 53 |
| 7 | 10 | 10 | 53 |
| 10 | 50 | 10 | 56 |
| Control | — | 10 | 25–30 |

EXAMPLE 3

The compounds Z-2-isovaleramido-2-butenoic acid, Compound 7, and Z-2-(2,2-dimethylcyclopropanecarboxamido)-2-butenoic acid, compounds were studied, in more detail in vivo in combination with thienamycin (THM), in the mouse. The general test procedure was similar to that of Example 2. Results are summarized in Table III and Table IV.

TABLE III

Effect of Co-administered Z—2-Isovaleramidobutenoic acid (Compound I) on the Urinary Recovery of Thienamycin in the Mouse[a]

| Route[b] | | mg/kg Dose | | Urinary Recovery |
|---|---|---|---|---|
| Compound 7 | THM | Compound 7 | THM | of THM, % |
| — | IV or SC | — | 10 | 30 ± 5 |
| SC | SC | 0.3 | 10 | 33 |
| SC | IV | 2 | 10 | 42 |
| SC | SC | 2 | 10 | 47 |
| SC | IV | 10 | 10 | 53 |
| SC | SC | 50 | 10 | 54 |
| SC | IV | 50 | 10 | 53 |
| SC | SC | 80 | 10 | 59 |
| SC | SC | 100 | 10 | 81 |

[a]20 g Charles River, $CD_1$ female mice
[b]Co-administered

TABLE IV

Effect of Co-administered Z—2-(2,2-Dimethylcyclopropanecarboxamido)-butenoic acid (Compound 2) on Urinary Recovery of Thienamycin in the Mouse[a]

| Route[b] | | mg/kg Dose | | Urinary Recovery |
|---|---|---|---|---|
| Compound 2 | THM | Compound 2 | THM | THM, % |
| — | SC | — | 10 | 30 ± 5 |
| SC | SC | 0.1 | 10 | 35 |
| SC | SC | 0.3 | 10 | 40 |
| SC | SC | 1 | 10 | 46 |
| SC | SC | 10 | 10 | 60 |
| SC | SC | 30 | 10 | 73 |

[a]20 g Charles River, $CD_1$ female mice
[b]Co-administered

EXAMPLE 4

In another mouse study, the systemic antibacterial activity of thienamycin was enhanced approximately three-fold by coadministering Z-2-isovaleramido-2-butenoic acid, see Table V.

TABLE V

Effect of Co-administered Z—2-Isovaleramido-2-butenoic acid on the Systemic Efficacy of Thienamycin on the Treatment of *Staphalococcus aureus* Infections

| THM | | ED$_{50}$, mg/kg |
|---|---|---|
| | Alone | 0.2 |
| | +100 mg/kg inhibitor | 0.06 |

EXAMPLE 5

A male beagle was used for a study of the effect of dipeptidase inhibitors on the urinary recovery of N-formimidoyl thienamycin. In a control study, the dog was given 5 mg/kg IV of the N-formimidoyl thienamycin without inhibitor. A second experiment used the same amount of N-formimidoylthienamycin, but also administered Z-2-isovaleramido-2-butenoic acid in 3 doses, each providing 20 mg/kg of the compound. The first dose was administered just after injection of the N-formimidoylthienamycin, the second at 40 min. and the third at 60 min. The third study employed a single dose (2 mg/kg) of Z-2-(2,2-dimethylcyclopropanecarboxamido)-2-butenoic acid, administered just before injection of the N-formimidoyl thienamycin. The results are in Table VI.

TABLE VI

Urinary Recovery 3 Hours Following the Administration of N—formimidoylthienamycin (5 mg/kg IV) in a Male Beagle

| Test Compound | % Urinary Recovery |
|---|---|
| N—formimidoyl thienamycin | 7.8 |
| plus Z—2-isovaleramido-2-butenoic acid | 46 |
| plus Z—2-(2,2-dimethylcyclopropane carboxamido)-2-butenoic acid | 53 |

EXAMPLE 5A

An in vivo assay is conducted using 34 Charles River CD female mice. Seventeen of the mice are administered 40 mg/kg of the inhibitor 7-(L-2-amino-2-carboxyethylthio)-2-(2,2-dimethylcyclopropanecarboxamido)-2-heptenoic acid subcutaneously, and an additional 40 mg/kg per os. Immediately thereafter they and an additional 17 mice are administered 10 mg/kg of the thienamycin class compoud (±)-[5R,6S]-2-ethylthio-6[(R)-1-hydroxyethyl]-pen-2-em-3-sodiocarboxylate by oral gavage. The level of the latter compound in plasma is tested at 10, 30, 60 and 90 minutes using 3 mice from each group at each time period. The following data are obtained.

| Time (minutes) | Plasma Level (mg/ml) Thienamycin Class Compound Alone | Thienamycin Class Compound Plus Inhibitor |
|---|---|---|
| 10 | 3.1 | 2.6 |
| 30 | 3.7 | 4.8 |
| 60 | 4.4 | 6.1 |
| 90 | 1.8 | 3.8 |

The remaining 5 mice from each group are tested for urinary recovery of the thienamycin class compound with the following results.

| Time After Administrator | % Urinary Recovery | |
|---|---|---|
| | Thienamycin Class Compound Plus Inhibitor | Thienamycin Class Compound Alone |
| 1 hour | 1.5% | 1.8% |
| 3 hours | 2.3% | 0.6% |
| Total | 3.8% | 2.4% |

Section 2. Examples Illustrating Chemical Preparations

The inhibitor compounds are novel compounds claimed in a copending application. These compounds are made by condensing directly the appropriate 2-keto acid and amide

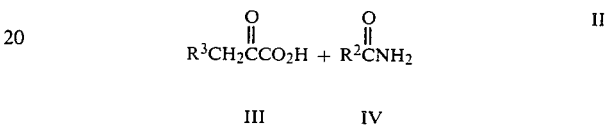

wherein $R^2$ and $R^3$ are as defined. The general reaction conditions involve mixing approximately 1-4:1 parts of the acid to the amide in an inert solvent such as toluene or methyl isovalerate and heating at reflux with azeotropic removal of water for from 3-48 hours, preferably 5-24 hours. The solution when cooled normally yields the product in crystalline form, but the product can also be isolated using a base extraction process. The product can be recrystallized by using generally known techniques. An optional modification of this procedure requires an additional small amount of p-toluenesulfonic acid as catalyst during the reaction.

Another route to the novel inhibitor compounds uses an α-amino acid, t-butyl ester in reaction with an acid chloride:

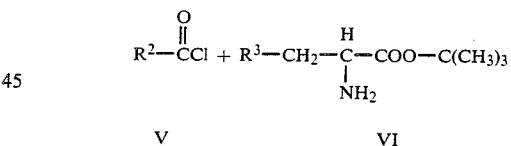

This reaction takes place in the presence of base, such as triethylamine, in a solvent such as methylene chloride. The resulting N-acylated product (VII) is then oxidized by treatment with t-butyl hypochlorite followed by addition of sodium methoxide. This yields the 2-methoxy derivative (VIII) and/or its elimination product, the α,β-unsaturated ester (IX). Further treatment with anhydrous hydrochloric acid converts either VIII or IX (or the mixture of both) to the desired α,β-unsaturated free acid (II).

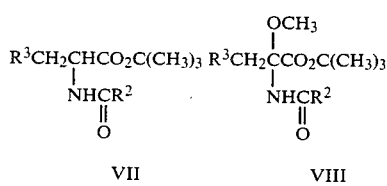

-continued

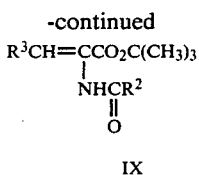

IX

Some compounds wherein $R^3$ has a terminal substituent which is an amino, quaternary nitrogen, thiol or carboxyl, derivative can be made most conveniently from an intermediate having a terminal bromine. In this case the intermediate has the structure

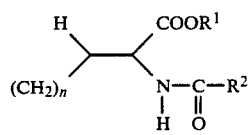

X wherein n is the number of carbons in the desired hydrocarbon chain (e.g., from 3–7).

In order to prepare $R^3$ having a terminal trimethylammonium substituent, the bromo intermedaite is reacted with trimethylamine; to yield the amino, the bromo intermediate is reacted with ammonia; the guanidino, reaction is with guanidine; to prepare the thio derivatives, including 2-amino-2-carboxxethylthio, the bromo compound is reacted with cysteine HCl, or the appropriate mercaptan. Derivatized amino, such as formamidino, ureido, and acylamide (acetamido) can be made from the compounds having an amino group by reacting with o-benzyl formimidate HCl, potassium cyanate and the appropriate acyl anhydride (acetic anhydride) respectively.

Another route for preparing compounds when $R^3$ is a terminally substituted thio devative utilizes a chloro-keto ester intermediate:

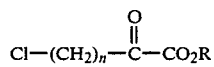

XI in reaction with the desired amide,

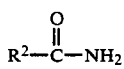

IV in toluene at reflux in the presence of a catalytic amount of p-toluenesulfonic acid. The resulting intermediate is hydrolyzed to the acid; the chloro group is then displaced in reaction with the appropriate mercaptan. This reaction is valuable since it permits use of the chiral amide IV, thereby preparing a functionalized side chain. In addition, the mixture of Z+E isomers prepared after the mercaptan condensation can be directly isomerized into the Z form by adding acid to a pH about 3, and heating to about 90° C. for 30 minutes. Only the Z form remains, and recovery is simple and straight forward.

More detail about preparation of the compounds is found in the following examples.

EXAMPLE 6

Z-2-Isovaleramido-2-butenoic Acid

A solution of 1.07 g (10.5 mmole) of 2-ketobutyric acid and 0.71 g (7.0 mmole) of isovaleramide in 15 ml of toluene was stirred under reflux with collection of $H_2O$ in a small Dean-Stark trap. After 5 hrs, the solution was cooled, resulting in fairly heavy crystallization. After standing, the solid was collected on a filter and washed with toluene and then with $CH_2Cl_2$. Yield of white crystals=0.47 g, mp 172°–174° (slight prelim. softening). The material was recrystallized from diisopropyl ketone. Tlc (4:1 toluene-AcOH) now showed only a faint trace of the other isomer. Yield of white crystals=0.32 g (25%), mp 175° (slight prelim. softening). NMR indicated essentially exclusively Z-isomer.

| Anal. ($C_9H_{15}NO_3$) | Calcd. | Found |
| --- | --- | --- |
| C | 58.36 | 58.59 |
| H | 8.16 | 8.55 |
| N | 7.56 | 7.43 |

EXAMPLE 7

Z-2-(2,2-Dimethylcyclopropanecarboxamido)-2-pentenoic acid

A solution of 1.74 g (15 mmole) of 2-ketovaleric acid and 1.13 g (10 mmole) of 2,2-dimethylcyclopropanecarboxamide in 20 ml of toluene was refluxed with stirring with collection of $H_2O$ in a small Dean-Stark trap. After 20 hrs. the solution was cooled and treated with a gentle stream of $N_2$. Before much of the solvent had evaporated, crystallization was induced by scratching. After standing, the solid was collected on a filter and washed with toluene and some $Et_2O$. Yield of white crystals=0.63 g (30%), mp 154.5°–155.5° (slight prelim. softening). Tlc (4:1 toluene-AcOH) showed only an extremely faint trace of the other isomer. NMR was consistent with the Z-configuration.

| Anal. ($C_{11}H_{17}NO_3$) | Calcd. | Found |
| --- | --- | --- |
| C | 62.53 | 62.86 |
| H | 8.11 | 8.27 |
| N | 6.63 | 6.75 |

EXAMPLE 8

Z-2-(3-Cyclopentylpropionamido)-2-butenoic acid

A solution of 1.41 g (10 mmole) of 3-cyclopentylpropionamide and 1.53 g (15 mmole) of 2-ketobutyric acid was stirred and refluxed under a small Dean-Stark trap. After 8 hrs the solution was cooled, resulting in heavy crystallization. The solid was collected on a filter and washed with toluene and $CH_2Cl_2$. Yeld of white crystals=1.44 g, mp 180.5°–182° (prelim. softening). The material was recrystallized from methyl ethyl ketone. Yield of white needles=0.63 g (28%), mp 184°–185° (slight prelim. softening). Tlc (4:1 toluene-AcOH) now showed a single spot, and NMR indicated essentially pure Z-isomer.

| Anal. ($C_{12}H_{19}NO_3$) | Calcd. | Found |
| --- | --- | --- |
| C | 63.97 | 63.99 |
| H | 8.50 | 8.67. |
| N | 6.22 | 6.27 |

EXAMPLE 9

Z-2-(2-Ethylhexanamido)-2-butenoic acid 10 g. of 2-ethylhexanoyl chloride was added dropwise with stirring to 25 ml of cold conc. NH4OH solution, resulting in immediate precipitation. The mixture was allowed to stir for 2 hrs., then filtered, and air dried to give 6.5 g. of amide. 1.4 g (10 mmole) of the above compound and 1.5 g of ketobutyric acid (15 mmole) were refluxed in 25 ml toluene for 15 hrs with removal of water. The reaction mixture was cooled and partly evaporated with a stream of $N_2$. Crystallization of product occurred after standing for 3 hrs. The crystals were collected, washed 3× with toluene, and air dried. There was isolated 1.13 g (50%) of product, mp 160°–162°. NMR was in accord with the assigned structure and indicated <5% E isomer. Tlc (4:1 toluene-AcOH) showed a single spot.

| Anal. ($C_{12}H_{21}NO_3$) | Calcd. | Found |
| --- | --- | --- |
| C | 63.40 | 63.63 |
| H | 9.30 | 9.43 |
| N | 6.16 | 5.88 |

EXAMPLE 10

Z-2-(2,2-Dimethylcyclopropanecarboxamido)-2-butenoic acid 1.53 g (15 mmoles) of 2-ketobutyric acid, 1.13 g (10 mmoles) of 2,2-dimethylcyclopropanecarboxamide and 20 ml of toluene stirred at reflux for 10 hours. After cooling the crystalline solid was filtered and washed with toluene (3×10 ml) and dried to give 1.06 g of product, mp 140°–141° C. Tlc (4:1 toluene-AcOH) showed essentially one spot and the NMR spectrum fit the desired structure.

Recrystallization from EtOAc gave after drying 0.533 g of product mp 142°–143.5°, homogeneous by tlc.

| Anal. ($C_{10}H_{15}NO_3$) | Calcd. | Found |
| --- | --- | --- |
| C | 60.90 | 60.92 |
| H | 7.67 | 7.71 |
| N | 7.10 | 7.38 |

EXAMPLE 11

Z-2-(2,2-Dimethylcyclopropanecarboxamido)-2-hexenedioic acid

A mixture of 1.0 g of 2,2-dimethylcyclopropanecarboxamide, 2.4 g. of 2-ketoadipic acid and 25 ml. of methyl isovalerate was heated under reflux for 4 hrs, with removal of $H_2O$ by a modified Dean-Stark trap containing molecular sieves (4A). After standing at room temperature overnight, the crystalline precipitate was filtered, washed with ether and recrystallized from ethyl acetate to give 0.23 g. of product, m.p. 163°–165°. The NMR spectrum was consistent with the desired structure.

| Anal. ($C_{12}H_{17}NO_5$) | Calcd. | Found |
| --- | --- | --- |
| C | 56.46 | 56.20 |
| H | 6.71 | 6.83 |
| N | 5.49 | 5.32 |

EXAMPLE 12

Z-2-(2,2-Diethylcyclopropanecarboxamido)-2-butenoic acid

A mixture of 2.3 g of 2-ketobutyric acid, 2.0 g of 2,2-diethylcyclopropanecaboxamide, and 25 ml of toluene was heated under reflux for 16 hrs with removal of H20 by a modified Dean-Stark trap containing molecular sieves (4A). No product precipitated upon cooling. Ether (25 ml) was added and the mixture was extracted with saturated $NaHCO_3$ (3 times). The combined extracts were acidified with concentrated HCl. The gummy precipitate crystallized when triturated with water. Recrystallization from ethyl acetate gave 0.31 g of product, m.p. 129°–30°. The NMR spectrum was consistent with the desired structure.

| Anal. ($C_{12}H_{19}NO_3$) | Calcd. | Found |
| --- | --- | --- |
| C | 63.98 | 64.01 |
| H | 8.50 | 8.62 |
| N | 6.22 | 6.21 |

EXAMPLE 13

2-(2,2-Dimethylcyclopropanecarboxamido)-2-hexenoic acid

Step A: DL-Norleucine t-butyl ester

General procedure of R. Roeske, *J. Org. Chem.* 28, p. 1251 (1963).

To a suspension of 9.82 g (75 mmole) of DL-norleucine in 80 ml of dioxane in a 500 ml. pressure bottle cooled in an ice bath was added slowly (with swirling) 8 ml of concentrated $H_2SO_4$. The resulting mixture was cooled in a dry ice bath as 80 ml of liquid isobutylene was added. The mixture was allowed to warm to room temperature and shaken under autogenous pressure for ~23 hrs. After most of the isobutylene had been vented off, the slightly hazy solution was cooled in ice and then added to a cold mixture of 400 ml of 1 N NaOH and 500 ml of $Et_2O$. After shaking in a separate funnel, the layers were separated, and the aqueous fraction was washed with an additional 100 ml of $Et_2$). The $Et_2O$ solution was shaken with 150 ml of 0.5 N HCl. The acidic aqueous fraction was treated with 2.5 N NaOH until strongly basic and then shaken with 250 ml of $Et_2O$. The $Et_2O$ solution was dried ($MgSO_4$), filtered, and concentrated on the rotovac. After prolonged pumping on high vacuum over a steam bath, final yield of clear, colorless residual oil=9.04 g (65%). NMR now showed only a trace of dioxane. TLC (9:1 $CHCl_3$-MeOH) showed a single spot.

Step B: N-(2,2-Dimethylcyclopropanecarbonyl)-DL-norleucine t-butyl ester

To a solution of 8.98 g (48 mmole) of DL-norleucine t-butyl ester and 5.05 g (50 mmole) of triethylamine in 100 ml of $CH_2Cl_2$ stirred in an ice bath under a drying tube was added dropwise (over a period of 75 min.) a solution of 6.39 g (48 mmole) of 2,2-dimethylcyclopropanecarbonyl chloride (M. Elliot and N. R. James, British Pat. No. 1,260,847 (1972)) in 50 ml of CH$_2$Cl$_2$. Precipitation of Et$_3$N HCl occurred during the addition, especially toward the end. As the ice gradually melted, the mixture was allowed to warm to room temperature. After 16 hrs, the mixture was shaken with 200 ml of 0.5 N HCl. The CH$_2$Cl$_2$ fraction was washed with an additional 200 ml of 0.5 N HCl, then with 2×200 ml of 0.5 N NaOH, and finally 200 ml of H$_2$O. The CH$_2$Cl$_2$ fraction was dried with MgSO$_4$, treated with charcoal, and filtered through Celite. The filtrate was concentrated on the rotovac (finally under high vacuum). Yield of light orange residual oil=11.93 g (88%). Tlc (2:1 hexane-EtOAc) showed a single spot. NMR and IR were in accord with the assigned structure. After standing for several days, the unused poriotion of this material crystallized: m.p. 52->65°.

Step C: t-Butyl 2-(2,2-dimethylcyclopropanecarboxamido)-2-methoxyhexanoate

Based on procedure of H. Poisel and V. Schmidt, *Chem. Ber.*, 108 p. 2547 (1975).

To a solution of 6.37 g (22.5 mmole) of N-(2,2-dimethylcyclopropanecarbonyl)-DL-norleucine t-butyl ester in 35 ml of Et$_2$O stirred at room temperature under N$_2$ in the dark was added 2.69 ml (2.45 g, 22.5 mmole) of t-butyl hypochlorite. After 15 min., a solution of sodium methoxide prepared by dissolving 0.52 g (22.6 mmole) of sodium in 35 ml of MeOH was added. Stirring was continued at ambient temperature under N$_2$ in the dark. After 16.5 hrs., the precipitated NaCl was filtered off. The filtrate was diluted with Et$_2$O and washed successively with 3×50 ml of 0.5 N HCl, 50 ml of saturated Na$_2$CO$_3$, and 2×50 ml of H$_2$O. The Et$_2$O phase was dried over MgSO$_4$ and filtered. The filtrate was concentrated on the rotovac. The pale, golden-yellow residual oil (6.45 g) was subjected to preparative high pressure liquid chromatography, resulting in the separation and isolation of 273 mg and 496 mg of the two diastereomers of t-butyl 2-(2,2-dimethylcyclopropanecarboxamido)-2-methoxyhexanoate (respective mp's 114°-118° and 124°-125.5°) as well as 1.97 g of a single isomer (apparently Z) of t-butyl 2-(2,2-dimethylcyclopropanecarboxamido)-2-hexenoate (colorless oil).

Step D: 2-(2,2-Dimethylcyclopropanecarboxamido)-2-hexenoic acid

A solution of 0.84 g (3.0 mmole) of t-butyl 2-(2,2-dimethylcyclopropanecarboxamido)-2-hexenoate in 10 ml of Et$_2$O saturated with anhydrous HCL was allowed to stand at room temperature under a drying tube. After 17 hrs, the solution was evaporated, and the residual gum was dissolved in 10 ml of saturated NaHCO$_3$. This solution was washed with an additional 15 ml of 0.5 N HCl, then dried (MgSO$_4$), filtered, and concentrated to give a viscous oil. The oil was crystallized from toluene. Yield of white crystals=0.32 g (47%), m.p. 119°-122°. TLC (4:1 toluene-AcOH) showed a single spot. NMR indicated essentially pure Z-isomer (Note: Treatment of the methanol adduct, t-butyl 2-(2,2-dimethylcyclopropanecarboxamido)-2-methoxyhexenoate, with anhydrous HCl in Et$_2$O under similar conditions gave the same product.)

EXAMPLE 14

(+)-Z-2-(2,2-Dimethylcyclopropanecarbonylamino)-2-octenoic acid, sodium salt

The reagents, (+)-2,2-dimethylcyclopropanecarboxamide, 7.0 g.; 2-keto-octanoic acid ethyl ester, 14.7 g.; 50 mg. of p-toluene sulfonic acid; and 100 ml. of toluene was changed to a 250 ml three-necked flask under a Dean Stark trap containing several molecular sieve pellets. The mixture was refluxed vigorously for 27 hours. The resultant light yellow solution was cooled and concentrated in vacuo, at a water bath temperature of 45° C., in the presence of water to help remove toluene. The gummy residue was suspended in 230 ml. of 2N NaOH and stirred at 30° C. for 3 hours; then the temperature was raised to 35° C. for an additional 2½ hrs. until a clear solution formed. The solution was then cooled, 85 ml. methylene chloride added, and the pH adjusted to 8.5 using 4N HCl with stirring. The organic layer was separated and discarded. The aqueous layer (366 ml. ) was assayed by liquid chromatography to contain 37.2 mg/ml; 87% Z isomer. Another 85 ml. portion of CH$_2$Cl$_2$ was then added and pH adjusted to 4.5 with stirring. The organic layer was separated and the aqueous layer reextracted with 50 ml. of CH$_2$Cl$_2$, with the pH again adjusted to 4.5. Combined organic extracts were dried over Na$_2$SO$_4$, filtered, and concentrated to a gum. This residue was dissoed in 150 ml. isopropanol and 15 ml water and the pH adjusted to 8.2 with 2 N NaOH. The resulting solution was concentrated to an oily residue which was flushed with isopropanol until it turned to a crystalline solid, indicating that most water had been removed. It was crystallized from 120 ml of isopropanol, (cooled in ice for 1 hour) filtered, and washed with 50 ml. cold isopropanol followed by copious amounts of acetone. It was dried at 60° C./0.1 mm/2 hours to yield 10.74 g (63.2%) crystalline material, having essentially a single peak in liquid chromatography, m.p. 241°-243° C.

The starting material, (+)-2,2-dimethylcyclopropanecarboxamide is most conveniently prepared by resolution of the D,L aid, followed by reaction with oxalyl chloride and then ammonia to give the resolved amide.

One way of making the starting material is as follows: 23.1 g. of D,L-2,2-dimethylcyclopropanecarboxylic acid was suspended in 33 ml H$_2$O and the pH adjusted to 8.0, using 50% NaOH, about 10 ml. To this was added a solution of 38.4 g quinine in a mixture of 60 ml methanol and 30 ml. H$_2$O to which had been added about 8 ml of concentrated HCl in another 30 ml. H$_2$O to give a pH of 7.1. (This was actually a solution of quinine hydrochloride.)

These solutions were added all at once, with stirring. The gummy crystalline material which formed was heated to give two clear layers and again stirred vigorously while cooling to give a crystalline product. This product was permitted to stand over two days at room temperature. It was then filtered, washed with 2×10 ml water, and 2×10 ml 50% methanol, and air dried with suction. The yield of crude quinine salt was 44.8 g (48.7% yield) monohydrate, m.p. 113°-116° C., having a $[\alpha]_D^{20}$ of −94.3°, C=1.0; CHCl$_3$. This material was recrystallized from acetone to yield 24.35, g, m.p. 127°-130° C. This purified quinine salt was converted to the acid by reaction with aqueous base and chloroform, followed by acid, to yield (96%) 3.9 g having $[\alpha]_D^{20}$ of +146.0°.

This acid was converted to the amide as follows: A charge of 30.5 g (+)acid was added over 5–10 minutes through a dropping funnel to chilled (10° C.) oxalyl chloride, 54 ml., containing 1 drop dimethylformamide. This was stirred overnight at ambient temperature. A clear solution was observed, which was added to 100 ml. methylene chloride to dilute. Excess oxalyl chloride was removed by concentrating and the mixture flushed twice with methylene chloride.

The resultant solution was diluted with an equal volume of methylene chloride, and added continuously through a dropping funnel to about 100 ml. anhydrous liquid ammonia which was diluted with 100 ml methylene chloride. A dry ice-acetone cooling bath was used during the addition. When all was added, the cooling bath was removed and the mixture stirred at room temperature for about ½ hour. The mixture was filtered, to remove precipitated ammonium chloride, and concentrated to dryness. The crude weight was 26.6 g. (88%). It was redissolved in excess hot ethyl acetate and filtered through a preheated sintered glass funnel to separate from trace NH₄Cl. Excess ethyl acetate was atmospherically distilled off. When half the volume remained, 130 ml of heptane were added, and ethyl acetate was continued to be distilled off, until the boiling point started to rise (to near 80° C.; much of product had already crystallized out). Heat was removed, and the mixture let cool gradually to about 30° C., then cooled with an ice bath to 0°–5° C. for about ½ hour. The product was recovered as nice silvery-white crystalline flakes, washed with 3×ethyl acetate/hexane mixture, 1/1.5 and air dried to constant weight. It weighed 23.3 g (77.1% yield overall, 87.6% recovery from crude), m.p.=135°–138° C. (varies with rate of heating). Angle of rotation was determined by dissolving 0.0543 g in 10 ml chloroform, $[\alpha]_D^{20}$=+100.9°.

EXAMPLE 15

Z-2-(2,2-Dichlorocyclopropanecarboxamido)-2-butenoic acid

Step A: 2,2-Dichlorocyclopropanecarboxamide

A 7.1 g sample of 2,2-dichlorocyclopropanecarbonyl chloride (U.S. Pat. No. 3,301,896, issued Jan. 31, 1967) was added dropwise to 75 ml of concentrated ammonium hydroxide with vigorous stirring. The temperature of the reaction mixture was maintained below 10° C. with an ice bath. The mixture was stirred in the ice bath for 30 min., then at room temperature for 1 hr. The aqueous ammonia was evaporated under reduced pressure (bath at 50° C.). The solid residue was extracted with hot ethyl acetate (3×30 ml). The extracts were boiled down to 40 ml and 20 ml of hexane was added. After cooling in ice, the solid was filtered, washed with ethyl acetate-hexane (1:1) and dried to give 2.7 g of 2,2-dichlorocyclopropanecarboxamide, m.p. 144°–146°. The NMR spectrum was in accord with the desired structure.

| Anal. (C₄H₅Cl₂NO) | Calcd. | Found |
| --- | --- | --- |
| C | 31.20 | 31.26 |
| H | 3.27 | 3.31 |
| N | 9.10 | 9.11 |
| Cl | 46.04 | 45.79 |

Another 1.3 g of amide, m.p. 143°–145° could be recovered from the mother liquor.

Step B:

Z-2-(2,2-Dichlorocyclopropanecarboxamido)-2-butenoic acid

A mixture of 1.53 g (15 mmoles) of 2-ketobutyric acid, 1.54 g (10 mmoles) of 2,2-dichlorocyclopropanecarboxamide and 10 ml of toluene was heated under reflux for 12 hrs. with removal of H₂O by a modified Dean-Stark trap containing molecular sieves (4A). An additionl 0.7 g of 2-ketobutyric acid was added and the reaction mixture was heated under reflux for an additional 12 hrs. The mixture was cooled, diluted with 20 ml of toluene and extracted with saturated sodium bicarbonate (3×10 ml). The extracts were combined, washed with ether and acidified to pH 3 (pH meter) with concentrated hydrochloric acid. A gum precipitated which soon solidified. It was filtered, washed with water, dried and recrystallized from nitromethane to give 423 mg of Z-2-(2,2-dichlorocyclopropanecarboxamido)-2-butenoic acid, m p. 188°–189.5° C. The NMR spectrum was in accord with the desired structure.

| Anal. (C₈H₉Cl₂NO₃) | Calcd. | Found |
| --- | --- | --- |
| C | 40.36 | 40.48 |
| H | 3.81 | 3.80 |
| N | 5.88 | 5.91 |
| Cl | 29.78 | 29.53 |

EXAMPLE 16

Z-2-(2,2-Dichlorocyclopropanecarboxamido)-2-octenoic acid

A mixture of 1.19 g (7.5 mmoles) of 2-ketooctanoic acid, 0.77 g (5.0 mmoles) of 2,2-dichlorocyclopropanecarboxamide, and 5 ml toluene were reacted using the same procedure as in the previous example. The crude product (537 mg) was purified by conversion to the methyl ester (BF₃/CH₃OH), preparative TLC (silica gel G, 4:1 hexane-EtOAc) and saponification of the pure Z-methyl ester (0.3M LiOH/CH₃OH) to give 88 mg of Z-2-(2,2-dichlorocyclopropanecarboxamido)-2-octenoic acid as a partially crystalline gum. NMR spectrum (DMSO-d₆):

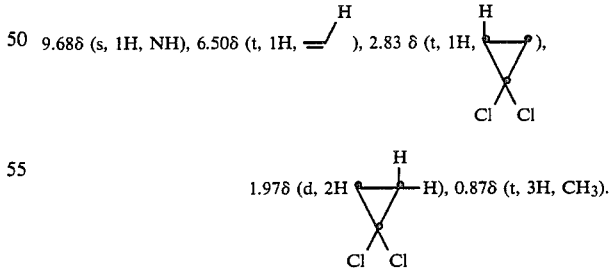

9.68δ (s, 1H, NH), 6.50δ (t, 1H, ), 2.83 δ (t, 1H, ), 1.97δ (d, 2H ―H), 0.87δ (t, 3H, CH₃).

EXAMPLE 17

Z-8-Bromo-2-(2,2-Dimethylcyclopropanecarboxamido)-2-octenoic acid

To a suspension of 14.4 g (0.3 mole) of 50% NaH dispersion in 360 ml of toluene cooled in an ice bath and in a N₂ atmosphere was added over 45 min. a solution of 146 g (0.6 moles) of 1,6-dibromohexane and 57.6 g (0.3 mole) of ethyl 1,3-dithiane-2-carboxylate in 120 ml of DMF. The cooling bath was removed and the mixture stirred at room temperature for 20 hrs. The reaction mixture was washed with water (3×210 ml), dried over MgSO₄ and evaporated under reduced pressure to give 179.5 g of a yellow oil containing the desired alkylated dithiane, 1,6-dibromohexane and mineral oil. This crude material was used in the next reaction without purification.

To a suspension of 46 g (2.4 moles) of N-bromosuccinamide in 800 ml of acetonitrile and 200 ml of H₂O was added over 45 min. a solution of the crude dithiane in 100 ml of acetonitrile. The temperature of the reaction mixture was maintained below 25° C. with an ice bath. After stirring at 20° C. for 10 min. the dark red reaction mixture was poured into 2 l. of hexane-CH₂Cl₂ (1:1). The solution was shaken with saturated NaHSO₃ (2×400 ml) and water (1×500 ml). Then 400 ml of saturated Na₂CO₃ solution was added in small portions (vigorous CO₂ solution). After the foaming subsided the funnel was shaken and the aqueous phase separated. The organic layer was extracted with saturated Na₂CO₃ solution (400 ml) and water (500 ml) and dried over MgSO₄. Removal of the solvent under reduced pressure gave 133.8 g of crude bromo ketoester containing 1,6-dibromohexane and mineral oil. This crude material was used in the next reaction without purification.

A mixture of 133.8 g of crude bromo ketoester, 133 ml of 50% hydrobromic acid and 267 ml of acetic acid was heated at 90° C. (internal temperature) for 75 min. The dark solution was evaporated under reduced pressure until most of the acetic acid was removed. The residue was dissolved in 500 ml of ether, washed with water (2×100 ml) and extracted with saturated NaHCO₃ (3×200 ml). The combined NaHCO₃ extracts were extracted with ether (2×100 ml) and acidified with concentrated HCl. The precipitated oil was extracted with ether (3×200 ml). The ether extracts were washed with water (1×100 ml) and saturated brine (1×100 ml) and dried over MgSO₄. Removal of the ether under reduced pressure gave 46.2 g of pure bromoketo acid Homogeneous by TlC (silica gel, 4:1 toluene-acetic acid). The NMR spectrum was consistent with the desired product.

A mixture of 46.1 g (0.194 moles) of the bromoketo acid, 17.6 g (0.156 mole) of 2,2-dimethylcyclopropanecarboxamide and 450 ml of toluene was heated under reflux for 13 hrs., with collection of water in a small Dean-Stark trap. After cooling, the clear reaction mixture was extracted with saturated NaHCO₃ solution (4×100 ml). The combined extracts were washed with ether (2×100 ml) and then the pH was adjusted to 3.5 (pH meter) by addition of concentrated HCl. An oil precipitated which soon crystallized. The solid was filtered, washed well with water and dried. Recrystallization from acetonitrile gave 22.5 g of Z-8-bromo-2-(2,2-dimethylcyclopropanecarboxamido)-2-octenoic acid, m.p. 151°–153° C. Homogeneous by TLC (4:1 tolueneacetic acid). The NMR spectrum was consistent with the desired structure.

| Anal. ($C_{14}H_{22}BrNO_3$) | Calcd. | Found |
|---|---|---|
| C | 50.61 | 50.66 |
| H | 6.67 | 6.96 |
| N | 4.22 | 4.45 |

-continued

| Anal. ($C_{14}H_{22}BrNO_3$) | Calcd. | Found |
|---|---|---|
| Br | 24.05 | 23.95 |

The following ω-bromo compounds were prepared using the same procedure:
Z-6-Bromo-2-(2,2-dimethylcyclopropanecarboxamido)-2-hexenoic acid;
Z-7-Bromo-2-(2,2-dimethylcyclopropanecarboxamido)-2-heptenoic acid;
Z-9-Bromo-2-(2,2-dimethylcyclopropanecarboxamido)-2-2-nonenoic acid;
Z-10-Bromo-2-(2,2dimethylcyclopropanecarboxamido)-2-decenoic acid;
Z-8-Bromo-2-(2,2-dichlorocyclopropanecarboxamido)-2-octenoic acid.

EXAMPLE 18

Z-8-Dimethylamino-2-(2,2-dimethylcyclopropanecarboxamido)-2-octenoic acid

A solution of 664 mg (2 mmoles) of Z-8-bromo-2-(2,2-dimethylcyclopropanecarboxamido)-2-octenoic acid in 10 ml of 40% aqueous dimethylamine was allowed to stand at room temperature for 4 hrs. The solution was poured onto a 3.5×20 cm column of Dowex 50 W-×8 (100–200 mesh, H+) ion exchange resin and the column eluted with water until the effluent was no longer acidic (~200 ml). The column was then eluted with 300 ml of 2 N ammonium hydroxide. The effluent was evaporated under reduced pressure to give 600 mg of a colorless glass. This material was dissolved in 3 ml of ethanol, filtered, and added dropwise to 200 ml of rapidly stirred acetone. A gummy solid precipitated which crystallized upon stirring for two days. The solid was filtered, washed with acetone, and dried to give 445 mg of Z-8-dimethylamino-2-(2,2-dimethylcyclopropanecarboxamido)-2-octenoic acid as colorless, hygroscopic crystals, m.p. 101°–112° C. Homogeneous by TLC (silica gel, in BuOH, HOAc, H₂O, 4:1:1). NMR spectrum was consistent with desired structure.

| Anal. ($C_{16}H_{28}N_2O_3 \cdot H_2O$) | Calcd. | Found |
|---|---|---|
| C | 61.12 | 61.03 |
| H | 9.62 | 9.28 |
| N | 8.91 | 8.67 |

The following ω-amino derivatives were prepared using essentially the same procedure.
Z-10-Dimethylamino-2-(2,2-dimethylcyclopropanecarboxamido)-2-decenoic acid;
Z-8-Amino-2-(2,2-dimethylcyclopropanecarboxamido)-2-octenoic acid;
Z-8-Dimethylamino-2-(2,2-dimethylcyclopropanecarboxamido)-2-octenoic acid;
Z-7-Dimethylamino-2-(2,2-dimethylcylclopropanecarboxamido)-2-heptenoic acid;
Z-2-(2,2-dimethylcyclopropanecarboxamido)-7-(N-methylpiperazinyl)-2-heptenoic acid;
Z-2-(2,2-dimethylcyclopropanecarboxamido)-8-pyrrolidino-2-octenoic acid;
Z-2-(2,2-dimethylcyclopropanecarboxamido)-8-(N-methylpiperazinyl)-2-octenoic acid;
Z-8-Allylamino-2-(2,2-dimethylcyclopropanecarboxamido)-2-octenoic acid;

Z-2-(2,2-dimethylcyclopropanecarboxamido)-8-piperidino-2-octenoic acid;

Z-2-(2,2-dimethylcyclopropanecarboxamido)-8-propargylamino-2-octenoic acid;

Z-8-N-[1-Deoxy-(1-methylamino)-D-glucityl]-2-(2,2-dimethylcyclopropanecarboxamido)-2-octenoic acid;

Z-8-(1-Adamantylamino)-2-(2,2-dimethylcyclopropanecarboxamido-2-octenoic acid;

Z-8-Diallylamino-2-(2,2-dimethylcyclopropanecarboxamido-2-octenoic acid;

Z-8-(2,2-dimethylcyclopropanecarboxamido)-8-(2-hydroxyethylmethylamino)-2-octenoic acid;

Z-8-[(Carboxylmethyl)methylamino]-2-(2,2-dimethylcyclopropanecarboxamido)-2-octenoic acid;

Z-2-(2,2-dimethylcyclopropanecarboxamido)-8-diethylamino-2-octenoic acid;

Z-2-(2,2-dimethylcyclopropanecarboxamido)-8-[tris(-hydroxymethyl)methylamino]-2-octenoic acid;

Z-2-(2,2-dimethylcyclopropanecarboxamido)-10-(N-methylpiperazinyl)-2-decenoic acid;

Z-2-(2,2-dimethylcyclopropanecarboxamido)-8-[1-(phosphono)ethylamino]-2-octenoic acid;

EXAMPLE 18A

Z-8-[(Carboxymethyl)methylamino]-2-(2,2-dimethylcyclopropane carboxamido)-2-octenoic acid 3.32 g of Z-8-bromo-2-(2,2-dimethylcyclopropane carboxamido)-2-octenoic acid, 1.0 g of $CH_3NH\ CH_2\text{-}CO_2H$, 3.5 g of $Na_2CO_3$ and 30 ml of water were heated at 80° C. in $N_2$ for 1.5 hours. After purification, 1.0 g of product was prepared, calc. for $C_{17}H_{28}N_2O_5 \cdot 2H_2O$: C, 54.24; H, 8.57; N, 7.44; found C, 54.40; H, 8.34; N, 7.16.

EXAMPLE 18B

Z-2-(2,2-dimethylcyclopropanecarboxamido)-8-[1-(phosphono)ethylamino-2-octenoic acid was prepared reacting the same bromo intermediate (335.1 mg) with 138.2 mg 1-aminoethane phosphoric acid, 435 mg $Na_2CO_3$ in 5 ml water, following essentially the same procedure, Ki=0.16.

EXAMPLE 19

Z-2-(2,2-Dimethylcyclopropanecarboxamido)-8-methylthio-2-octenoic acid.

A stream of $CH_3SH$ gas was bubbled through a solution of 162 mg (3 mmoles) of sodium methoxide in 5 ml of methanol for 10 min. with cooling in an ice bath. The solution was allowed to warm to room temperature and 332 mg (1 mmole) of Z-8-bromo-2-(2,2-dimethylcyclopropanecarboxamido)-2-octenoic acid was added. The solution was heated under reflux for 30 min. in a $N_2$ atmosphere. Most of the methanol was evaporated under reduced pressure, the residue 2.5 N HCl. The precipitated oil was extracted with ether (3×). The ether extracts were washed with water, saturated brine and dried over $MgSO_4$. Removal of the ether under reduced pressure gave a colorless oil that crystallized upon standing. It was recrystallized from ether-hexane to give 178 mg of Z-2-(2,2-dimethylcyclopropanecarboxamido)-8-methylthio-2-octenoic acid, m.p. 82°–84° C. Homogeneous by TLC (toluene-acetic acid, 4:1). The NMR spectrum was in accord with the desired structure

| Anal. ($C_{15}H_{25}NO_3S$) | Calcd. | Found |
|---|---|---|
| C | 60.18 | 60.36 |

| Anal. ($C_{15}H_{25}NO_3S$) | Calcd. | Found |
|---|---|---|
| H | 8.42 | 8.68 |
| N | 4.68 | 4.59 |
| S | 10.69 | 10.87 |

The following compounds were prepared by similar methods.

Z-2-(2,2-dimethylcyclopropanecarboxamido)-8-ethoxythiocarbonylthio-2-octenoic acid;

Z-2-(2,2-dimethylcyclopropanecarboxamido)-8-(1-methyl-5-tetrazolylthio)-2-octenoic acid;

Z-2-(2,2-dimethylcyclopropanecarboxamido)-7-{[(methoxycarbonyl)methyl]thio}-2-heptenoic acid;

Z-8-Acetylthio-2-(2,2-dimethylcyclopropanecarboxamido)-2-octenoic acid;

Z-7-[(2-Amino-2-oxoethyl)thio]-2-(2-dimethylcyclopropanecarboxamido)-2-heptenoic acid;

6-(L-2-Amino-2-carboxyethylthio)-2-(2,2-dimethylcyclopropanecarboxamido)-2-hexenoic acid;

Z-8-(Carbomethoxymethylthio)-2-(2,2-dimethylcyclopropanecarboxamido)-2-octenoic acid;

Z-6-(Carbomethoxymethylthio)-2-(2,2-dimethylcyclopropanecarboxamido)-2-hexenoic acid;

Z-2-(2,2-dimethylcyclopropanecarboxamido)-6-(phosphonomethylthio)-2-hexenoic acid.

The compound 7-(L-amino-2-carboxyethylthio)-2-(2,2-dimethylcyclopropanecarboxamido)-2-heptenoic acid is prepared in a similar fashion as the above example, except that Z-7-bromo-2-(2,2-dimethylcyclopropanecarboxamido)-2-heptenoic acid (prepared as in Example 17) (185 mg, 1.05 mmoles) is dissolved in 2.02 ml NaOH solution (2.0 N), and deoxygenated by bubbling a stream of nitrogen gas through it for a minute. Then cysteine.HCl (185 mg, 1.05 mmoles) is added all at once and the reaction stirred at room temperature in a $N_2$ atmosphere for 3 hours. The reaction mixture is applied to 2×20 cm column of Dowex 50×4 (100–200 mesh, H+), and eluted with 300 ml $H_2O$, then 200 ml of 2 N $NH_3$ solution. Ammonia evaporated under reduced pressure to give 284 mg of a yellowish glass. This product is dissolved in 4 ml ethanol, and the insoluble material filtered. The filtrate is added dropwise to rapidly stirred diethylether (150 ml). The solid which precipitates is filtered, washed with ether and dried to yield 171 mg product, having one spot (ninhydrin positive) in TLC ($\mu$BuOH, HOAc, $H_2O$; 4:1:1) rf. about 6; NMR is consistent with the desired structure.

| Anal. ($C_{16}H_{26}N_2O_5S$) | Calcd. | Found |
|---|---|---|
| C | 53.61 | 52.55 |
| H | 7.31 | 7.40 |
| N | 7.81 | 7.89 |
| S | 8.94 | 9.63 |

EXAMPLE 19A

Sodium Z-7-(L-amino-2-Carboxyethylthio)-2-(2,2-dimethylcyclopropane carboxamido)-2-heptenoic acid A. Grignard preparation of Ethyl-7-Chloro-2-oxoheptanoate Equimolar amounts (8 moles each) of 1-bromo-5-chloropentane and magnesium are reacted in tetrahydrofuran (960 ml) at 25° C. The flask is charged with the Mg in the THF and the bromochloropentane added over 1 hour, then aged 2 hours. After the reaction was judged complete, the reaction solution was added (cooled −15° C., to 16 moles of diethyloxalate in 1856 ml tetrahydrofuran, while maintaining the temperature at 10° C. 3N HCl was added to quench, keeping the temperature below 25° C. After stripping solvents, the calculated yield is 48.8% of the ethyl-1-chloro-6-oxoheptenoate.

B. Condensation and Hydrolysis

S-2,2-dimethylcyopropyl carboxamide (1017 g), 2143.6 g of ethyl-7-chloro-2-ketoheptanoate, 9 liters of toluene and 12 g of p-toluene sulfonic acid were charged to a 22 L flask, and heated to reflux with stirring. After 23 hours, liquid chromatography showed the expected product ratio, and 4 L of toluene were removed under slightly reduced pressure. The pot was charged with water, neutralized to pH 7 with 2 N NaOH, and vacuum distilled leaving a final pot volume of about 5 liters.

This was hydrolyzed by adding 1760 g of 50% aq. NaOH (4 liters water) and stirring overnight. The flask was charged with 4 L methylene chloride, and pH adjusted to 8.8 using HCl. Unreacted amide crystallized out. The organic layers were separated from water, and then evaporated. The gummy residue was dissolved in 8 L water containing 720 g, 50% NaOH, and to this solution was charged 1818 g L-cysteine HCl.H$_2$O, 2 kg ice, 2484 g 50% NaOH and 1 L water.

The pH of this solution, after aging overnight at room temperature, is adjusted to 3.0 with conc. HCl, and the resulting gummy suspension heated to 95° C. to afford a clear solution. After 30 minutes, no E isomer could be detected by lc. After work-up and purification, the overall yield was 2060 g, 87% yield. This material was recrystallized from acetonitrile. 1500 g of the recrystallized material was dissolved in 6 L water and 910 ml 3.88 N NaOH, then neutralized to pH 7, and lyophilized to afford 1569 g (98.6%) of the title compound; Analysis: Calcd.: C, 50.52; H, 6.62; N, 7.36; S, 8.43; Na, 6.04: Found: C. 50.71; H, 6.78; N, 7.49; S, 8.52; Na 5.92.

EXAMPLE 19B

Z-8-[(2-Amino-2-oxoethyl)thio]-2-(2,2-dimethylcyclopropane carboxamide)-2-octenoic acid was also prepared in a similar manner, to that described in Example 19, above, using 3.3 gm of the bromo intermediate, 1.3 g of H$_2$NC(=O)CH$_2$SH, in 50 ml methanol. 1.6 gms of product, mp. 127°–128° C. was obtained.

EXAMPLE 20

Z-2-(2,2-Dimethylcyclopropanecarboxamido)-8-trimethylammonium hydroxide-2-octenoic acid inner salt A solution of 996 mg (3 mmoles)of Z-8-bromo-2-(2,2-dimethylcyclopropanecarboxamido)-2-octenoic acid in 15 ml of 25% aqueous trimethylamine was allowed to stand at room temperature for 3 hrs. The reaction mixture was poured onto a 2×25 cm column of IRA-410 (50–100 mesh, OH$^-$) ion exchange resin and eluted with water until the effluent was no longer basic. The effluent was evaporated under reduced pressure to give 800 mg of a colorless glass. This material was dissolved in 20 ml of ethanol, filtered and diluted with 600 ml of acetone. After standing at room temperature overnight the crystalline solid which deposited was filtered, washed with acetone and dried to give 720 mg of Z-2-(2,2-dimethylcyclopropanecarboxamido)-8-trimethylammonium hydroxide-2-octenoic acid inner salt as hygroscopic crystals, m.p. 220°–222° C. Homogeneous by TLC (silica gel, in BuOH, HOAc, H$_2$O, 4:1:1). NMR spectrum was consistent with desired structure.

| Anal. (C$_{17}$H$_{30}$N$_2$O$_3$) | Calcd | Found |
| --- | --- | --- |
| C | 65.77 | 65.78 |
| H | 9.74 | 9.98 |
| N | 9.02 | 8.92 |

Other quaternary derivatives were prepared using essentially the same procedure; these are Z-2-(2,2-Dimethylcyclopropanecarboxamido)-8-trimethylammonium hydroxide-2-octenoic acid inner salt;

Z-2-(2,2-Dimethylcyclopropanecarboxamido)-8-pyridinium hydroxide-2-octenoic acid inner salt;

Z-2-(2,2-Dimethylcyclopropanecarboxamido)-8-(2-hydroxyethyldimethylammonium hydroxide)-2-octenoic acid inner salt;

Z-2-(2,2-Dimethylcyclopropanecarboxamido)-10-trimethylammonium hydroxide-2-decenoic acid inner salt;

Z-8-(Benzyldimethylammonium hydroxide)-2-(2,2-dimethylcyclopropanecarboxamido)-2-octenoic acid inner salt;

Z-10-(Benzyldimethylammonium hydroxide)-2-(2,2-dimethylcyclopropanecarboxamido)-2-decenoic acid inner salt;

Z-2-(2,2-Dimethylcyclopropanecarboxamido)-9-trimethylammonium hydroxide-2-nonenoic acid inner salt;

Z-8-(2-Dimethylaminoethylammonium hydroxide)-2-(2,2-dimetlcyclopropanecarboxamido)-2-octenoic acid inner salt;

Z-2-(2,2-Dichlorocyclopropanecarboxamido)-8-trimethylammonium hydroxide-2-octenoic acid inner salt;

EXAMPLE 21

Z-2-(2,2-Dimethylcyclopropanecarboxamido)-8-5 formamidino-2-octenoic acid

A 350 mg sample of Z-8-amino-2-(2,2-dimethylcyclopropanecarboxamido)-2-octenoic acid was dissolved in 10 ml of water and the pH adjusted to 8.5 with 2.5 N NaOH. A total of 947 mg of benzyl formimidate hydrochloride was added at room temperature in small portions over 20 min. while the pH was maintained between 8–9 by addition of 2.5 N NaOH. After stirring at room temperature for 30 min., the cloudy reaction mixture was extracted with ether (3X) and applied to a 2×2.5 cm column of an AG50W-X4 (Na$^+$, 200–400 mesh) resin. After elution with water, the fractions containing the product were pooled and evaporated under reduced pressure. This material was dissolved in water and applied to a 2×25 cm column of an AG1X8 (HCO$_3$$^-$, 200–400 mesh) resin. After elution with water, the fractions containing pure product were pooled and evaporated under reduced pressure. The residue was dissolved in a few ml of warm ethanol, filtered, and added dropwise to 200 ml of ether with rapid stirring. Filtration and washing with ether gave 243 mg of Z-2-(2,2-dimethylcyclopropanecarboxamido)-8-formamidino-2-octenoic acid as an amorphous solid. Homongeneous by TLC (n-BuOH, HOAc, H$_2$O; 4:1:1). The NMR spectrum was in accord with the desired structure.

| Anal. ($C_{15}H_{25}N_3O_3 \cdot 1/3H_2O$) | Calcd. | Found |
|---|---|---|
| C | 59.69 | 60.04 |
| H | 8.59 | 8.64 |
| N | 13.92 | 13.57 |

The following amidino compounds were prepared using similar procedures:
Z-8-Acetamidino-2-(2,2-dimethylcyclopropanecarboxamido)-2-octenoic acid;
Z-8-N-Benzylformamidino-2-(2,2-dimethylcyclopropanecarboxamido)-2-octenoic acid;
Z-2-(2,2-Dimethylclopropanecarboxamido)-10-formamidino-2-decenoic acid;
Z-2-(2,2-Dimethylcyclopropanecarboxamido)-8-(2-imidazolinyl-amino)-2-octenoic acid.

EXAMPLE 22

Z-2-(2,2-Dimethylcyclopropanecarboxamido)-8-guanidino-2-octenoic acid

To a solution of 2 mmoles of guanidine (prepared from 432 mg of guanidine sulfate and 630 mg of barium hydroxide octahydrate) in 7 ml of water was added 332 mg (1 mmole) of 8-bromo-2-(2,2-dimethylcyclopropanecarboxamido)-2-octenoic acid, and the solution was heated at 70° C. in a nitrogen atmosphere for 1 hr. The reaction mixture was applied to a 2×25 cm column of Dowex 50W-X8 (H+, 100-200 mesh). After elution with water the fractions containing the product were pooled and evaporated under reduced pressure. The residue was dissolved in several ml of warm ethanol and added dropwise to 100 ml of ether with rapid stirring. Filtration and washing with ether gave 107 mg of Z-2-(2,2-dimethylcyclopropanecarboxamido)-8-guanidino-2-octenoic acid as an amorphous electrostatic powder. Homogeneous by TLC (n-BuOH, HOAc, $H_2O$; 4:1:1). NMR ($D_2O$, NaOD):

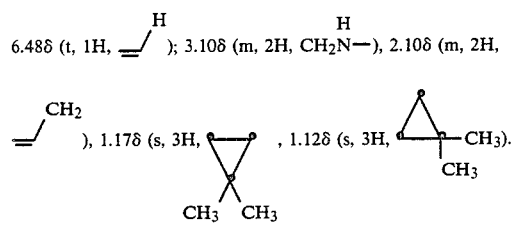

The following guanidino compound was prepared using the same procedure:
Z-2-(2,2-Dimethylcyclopropanecarboxamido)-8-(N,N-dimethylguanidino)-2-octenoic acid.

EXAMPLE 23

Z-2-(2,2-Dimethylcyclopropanecarboxamido)-8-methoxy-2-octenoic acid

To a solution of 2.43 mmoles of sodium methoxide in 5 ml of methanol was added 332 mg (1 mmole) of 8-bromo-2-(2,2-dimethylcyclopropanecarboxamido)-2-octenoic acid. The solution was heated under reflux in a nitrogen atmosphere for 1 hr. The reaction mixture was evaporated under reduced pressure, the residue dissolved in water and acidified with 2.5 N hydrochloric acid. The oil which precipitated was extracted with ether (3×). The ether extracts were washed with water, and saturated brine and dried over $MgSO_4$. Removal of the ether under reduced pressure gave a colorless oil that crystallized upon standing. It was recrystallized from ether-hexane to give 140 mg of Z-2-(2,2-dimethylcyclopropanecarboxamido)-8-methoxy-2-octenoic acid, m.p. 71°-72° C. Homogeneous by TLC (toluene-HOAc, 4:1). The NMR spectrum was in accord with the desired structure.

| Anal. ($C_{15}H_{25}NO_4$) | Calcd. | Found |
|---|---|---|
| C | 63.58 | 63.54 |
| H | 8.89 | 9.12 |
| N | 4.94 | 5.16 |

Using similar procedures, the following compounds were prepared:
Z-8-Cyano-2-(2,2-dimethylcyclopropanecarboxamido)-2-octenoic acid;
Z-7-Cyano-2-(2,2-dimethylcyclopropanecarboxamido)-2-heptenoic acid;
Z-9-Cyano-2-(2,2-dimethylcyclopropanecarboxamido)-2-nonenoic acid;
Z-2-(2,2-Dimethylcyclopropanecarboxamido)-7-sulfo-2-heptenoic acid sodium salt;
Z-2-(2,2-Dimethylcyclopropanecarboxamido)-8-sulfo-2-octenoic acid sodium salt;
Z-2-(2,2-Dimethylcyclopropanecarboxamido)-8-hydroxy-2-octenoic acid;
Z-8-Acetoxy-2-(2,2-dimethylcyclopropanecarbamido)-2-octenoic acid.

The Z-8-cyano-2-(2,2-dimethylcyclopropane carboxamido)-2-octenoic compound was prepared from 332 mg 8-bromo-2-(2,2-dimethylcyclopropane carboxamido)-2-octenoic acid and 100 mg NaCN in 2 ml DMSO, heated at 80° C. for 30 minutes. After extraction and purification, 102 mg of a colorless solid, mp 99°-103° C. were recovered, analysis for $C_{15}H_{22}N_2O_3$: Calcd.: C, 64.73; H, 7.97; N, 10.06: Found: C, 64.69; H, 8.14; N, 9.41.

What is claimed is:
1. A method for inhibiting the dipeptidase enzyme (E.C.3.4.13.11) which comprises administering to an animal from 3-200 mg/kg daily of a compound of the following formula:

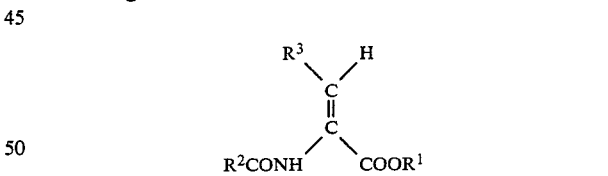

wherein $R^2$ and $R^3$ are hydrocarbon radicals in the range respectively of 3-10 and 1-15 carbon atoms; in either one of these $R^2$ or $R^3$ hydrocarbon chains 1-6 hydrogens may be replaced by halogens or a nonterminal methylene may be replaced by oxygen or sulfur, including oxidized forms of the latter; additionally, a terminal hydrogen in $R^3$ can also be replaced by hydroxyl or thiol, which may be acylated or carbamoylated; or the hydrogen can be replaced by amino, which may be derivatized as in an acylamino, ureido amidino, quanidino, or alkyl or substituted amino group, including quaternary nitrogen groupings; or, there may be replacement by acid groups such as carboxylic, phosphonic or sulfonic acid groups or esters or amides thereof, or cyano; or combinations thereof, such as a terminal amino acid grouping; and $R^1$ is hydrogen or lower alkyl (C$_{1-6}$) or dialkylaminoalkyl, or a pharmaceutically acceptable cation.

2. The method of claim 1 in which the dipeptidase inhibitor is 7-(L-2-amino-2-carboxyethylthio)-2-(2,2-dimethylcyclopropane carboxamido)-2-heptenoic acid.

3. The method of claim 1 wherein R$^2$ is branched alkyl or cycloalkyl with a limitation that the carbon adjacent to the carbonyl cannot be tertiary.

4. The method of claim 3 wherein R$^3$ is n-alkyl (1–9 carbons) or n-alkyl (1–9 carbons) having a terminal substituent which is a quaternary nitrogen, amine derivative or amino acid derived group.

5. The method of claim 4 wherein R$^2$ is 2,2-dimethyl cyclopropyl or 2,2-dichlorocyclopropyl and R$^3$ is a hydrocarbon chain of 3 to 7 carbon atoms without a terminal substituent or having a terminal substituent which trimethylammonium, amidino, guanidino or 2-amino-2-carboethylthio.

6. The method of claim 5 wherein said dipeptidase inhibitor is

Z-2-(2,2-dimethylcyclopropanecarboxamido)-8-trimethylammonium hydroxide-2-octenoic acid inner salt;

Z-2-(2,2-dichlorocyclopropanecarboxamido)-8-trimethylammonium hydroxide-2-octenoic acid inner salt;

Z-2-(2,2-dimethylcyclopropanecarboxamido)-8-guanidino-2-octenoic acid;

Z-2-(2,2-dimethylcyclopropanecarboxamido)-8-guanidino-2-octenoic acid;

Z-2-(2,2-dimethylcyclopropanecarboxamido)-8-ureido-2-octenoic acid;

Z-8-(1-2-amino-2-carboxyethylthio)-2-(2,2-dimethylcyclopropanecarboxamido)-2-octenoic acid;

Z-2-(2,2-dimethylcyclopropanecarboxamido)-2-octenoic acid (racemic and dextrorotatory forms);

Z-2-(2,2-dichlorcyclopropanecarboxamido)-2-octenoic acid;

7-(L-2-amino-2-carboxyethylthio)-2-(2,2-dimethylcyclopropanecarboxamido)-2-heptenoic acid; or 6-(L-2-amino-2-carboxyethythio)-2-(2,2-dimethylcyclopropanecarboxamido)-2-hexenoic acid.

* * * * *